US010377698B2

(12) United States Patent
Schmidhammer et al.

(10) Patent No.: US 10,377,698 B2
(45) Date of Patent: Aug. 13, 2019

(54) DIPHENETHYLAMINE DERIVATIVES WHICH ARE INTER ALIA USEFUL AS ANALGESICS AND METHOD FOR THEIR PRODUCTION

(71) Applicant: UNIVERSITY OF INNSBRUCK, Innsbruck (AT)

(72) Inventors: Helmut Schmidhammer, Innsbruck (AT); Mariana Spetea, Innsbruck (AT); Elena Guerrieri, Innsbruck (AT)

(73) Assignee: University of Innsbruck, Innsbruck (AT)

( * ) Notice: Subject to any disclaimer, the term of this patent is extended or adjusted under 35 U.S.C. 154(b) by 0 days.

(21) Appl. No.: 15/561,614

(22) PCT Filed: Mar. 30, 2016

(86) PCT No.: PCT/EP2016/056918
§ 371 (c)(1),
(2) Date: Sep. 26, 2017

(87) PCT Pub. No.: WO2016/156396
PCT Pub. Date: Oct. 6, 2016

(65) Prior Publication Data
US 2018/0072654 A1    Mar. 15, 2018

Related U.S. Application Data

(60) Provisional application No. 62/139,962, filed on Mar. 30, 2015.

(51) Int. Cl.
| | |
|---|---|
| *C07C 211/27* | (2006.01) |
| *C07C 255/58* | (2006.01) |
| *C07C 211/29* | (2006.01) |
| *C07C 211/52* | (2006.01) |
| *C07C 215/52* | (2006.01) |
| *C07C 215/64* | (2006.01) |
| *C07C 217/60* | (2006.01) |
| *C07C 217/74* | (2006.01) |
| *C07C 237/30* | (2006.01) |

(52) U.S. Cl.
CPC .......... *C07C 211/27* (2013.01); *C07C 211/29* (2013.01); *C07C 211/52* (2013.01); *C07C 215/52* (2013.01); *C07C 215/64* (2013.01); *C07C 217/60* (2013.01); *C07C 217/74* (2013.01); *C07C 237/30* (2013.01); *C07C 255/58* (2013.01)

(58) Field of Classification Search
CPC ... C07C 211/27; C07C 211/29; C07C 211/52; C07C 215/52; C07C 215/64; C07C 217/60; C07C 217/74; C07C 237/30; C07C 255/58; A61K 31/137; A61P 3/00; A61P 13/00; A61P 15/00; A61P 25/00; A61P 35/00; A61P 37/00
See application file for complete search history.

(56) References Cited

U.S. PATENT DOCUMENTS

| | | | | |
|---|---|---|---|---|
| 4,130,658 A | * | 12/1978 | Nedelec | A61K 31/195 514/567 |
| 5,102,759 A | * | 4/1992 | Fuse | G03G 5/0514 430/58.15 |
| 5,141,962 A | | 8/1992 | Cosquer | |
| 7,977,020 B2 | * | 7/2011 | Obata | C07C 211/28 399/119 |
| 8,168,826 B2 | * | 5/2012 | Coats | C07C 233/40 525/333.6 |

OTHER PUBLICATIONS

Layzer, Degenerative Diseases of the Nervous System, Cecil Textbook of Medicine, 20th Edition, vol. 2, pp. 2050-2057 (1996).*
Damasio, Alzheimer's Disease and Related Dementias, Cecil Textbook of Medicine, 20th Edition, vol. 2, pp. 1992-1996 (1996).*
Gura et al., Systems for identifying new drugs are often faulty, Science, 278:1041-1042, (1997).*
Johnson et al., Relationships between drug activity in NCI preclinical in vitro and in vivo models and early clinical trials, British Journal of Cancer, 84(10):1424-1431, (2001).*
Simone, Oncology: Introduction, Cecil Textbook of Medicine, 20th Edition, vol. 1, pp. 1004-101 O, (1996).*
Pearce et al., Failure modes in anticancer drug discovery and development, Cancer Drug Design and Discovery Edited by Stephen Neidle, Chapter 18, pp. 424-435 (2008).*
Spetea et al., Discovery and Pharmacological Evaluation of a Diphenethylamine Derivative (HS665), a Highly Potent and Selective κ Opioid Receptor Agonist, Journal of Medicinal Chemistry, 55, pp. 10302-10306 (2012).*
STN Registry (RN 1626686-95-0), Sep. 26, 2014.*
STN Registry (RN 1049694-55-4), Sep. 17, 2008.*
STN Registry (RN 1027560-30-0), Jun. 12, 2008.*
STN Registry (RN 857338-11-5), Jul. 28, 2005.*
STN Registry (RN 802579-04-0), Dec. 26, 2004.*
STN Registry (RN 757883-34-4), Oct. 6, 2004.*
STN Registry (RN 588709-09-5), Sep. 19, 2003.*
STN Registry (RN 7154-06-5), Nov. 16, 1984.*
STN Registry (RN 6271-34-7), Nov. 16, 1984.*

* cited by examiner

*Primary Examiner* — Deepak R Rao
(74) *Attorney, Agent, or Firm* — Cozen O'Connor

(57) ABSTRACT

Diphenethylamine derivatives for use as highly active analgesics, diuretics, anxiolytics, for the treatment of neurodegenerative, psychiatric and neuropsychiatric disorders, and also as anti-itch, anti-addiction, anti-inflammatory, anti-obesity, anti-epileptic, anti-convulsant, anti-seizure, anti-stress, anti-psychotic and anti-depressant medications and their pharmaceutically acceptable salts and easily accessible derivatives thereof (e.g. esters, ethers, amides), processes for their preparation and their application in the manufacture of pharmaceutical products.

13 Claims, No Drawings

DIPHENETHYLAMINE DERIVATIVES WHICH ARE INTER ALIA USEFUL AS ANALGESICS AND METHOD FOR THEIR PRODUCTION

FIELD OF THE INVENTION

The present invention relates to diphenethylamine derivatives which can be used as highly active analgesics, diuretics, anxiolytics, for the treatment of neurodegenerative, psychiatric and neuropsychiatric disorders, and also as anti-itch, anti-addiction, anti-inflammatory, anti-obesity, anti-epileptic, anti-convulsant, anti-seizure, anti-stress, anti-psychotic and anti-depressant medications and to their pharmaceutically acceptable salts and easily accessible derivatives thereof (e.g. esters, ethers, amides), to processes for their preparation and their application in the manufacture of pharmaceutical products.

BACKGROUND OF THE INVENTION

Opioids act on three G protein-coupled receptors (GPCRs) that is, μ (MOR), δ (DOR), and κ (KOR), but it appears that the analgesic action of many commonly used opioid analgesics is mediated primarily via the MOR. It is known that activation of MORs, which are widely expressed in the central nervous system (CNS), peripheral nervous system and peripheral tissues, is responsible not only for beneficial (analgesia) effects but also for a number of several centrally mediated adverse effects, which limits their clinical usefulness. Adverse effects associated with MOR opioid analgesics include respiratory depression, nausea, sedation, dizziness, vomiting, hypotension, and constipation. Long-term use of such opioids can cause tolerance, and thus complicating optimal pain treatment. Another concern with the prolonged use of opioids is physical dependence and development of addictive disorders. On the other hand, the therapeutic utility of the so far known KOR agonists is associated with dose-limiting effects including dysphoria, sedation and other neuropsychiatric adverse effects. Besides the analgesic activity, KOR agonists have also shown other beneficial actions such as anti-pruritic, anti-arthritic, anti-inflammatory, and neuroprotective effects.

As it is the case for other GPCRs, also for MOR, DOR and KOR agents with agonistic effects can be separated from those with antagonistic effects. An agonist is an agent that binds to a receptor and activates that receptor in order to mimic the action of the naturally occurring, endogenous transmitter-molecule. A therapeutically used agonist typically has the same or a stronger affinity to the respective receptor than the endogenous transmitter-molecule. An antagonist, on the other hand, is an agent that binds to a receptor but does not elicit the response that the endogenous transmitter-molecule would trigger. Instead, the antagonist blocks the receptor and prevents its activation by endogenous transmitter-molecules or agonistic drugs.

In the case of opioids, morphine, oxycodone or fentanyl, for example, act as classical agonists. When morphine enters the brain, it binds to opioid receptors and activates them. In case of a morphine overdose, where the high dose of morphine may cause respiratory depression and a drastic drop in blood pressure and heart rate, one may administer naloxone, an opioid antagonist. Naloxone competes with morphine for binding to the receptors, but with a higher affinity than morphine and thus, replaces much of the morphine at the respective receptors. In cases of opioid-addiction, naloxone can allay withdrawal symptoms (nausea, vomiting, hallucinations, tremors, anxiety, etc.). A third class of opioids comprises drugs acting as a partial agonist (or mixed agonists-antagonists) at a single receptor (e.g. buprenorphine) showing an analgesic ceiling effect. A fourth class includes drugs being an agonist or partial agonist at one receptor and an antagonist at another receptor (e.g. the weak MOR-antagonists and partial KOR agonists: pentazocine, butorphanol, nalbuphine). These drugs can be classified as nalorphine-like or morphine-like. And finally there are those, which do not fit into either classification and form a separate class (e.g. meptazinol).

There are three traditional types of pharmacotherapy of opioid addiction (i) antagonists that bind to the opioid receptors with higher affinity than agonists but do not activate the receptor (e.g. naloxone or naltrexone), (ii) agonist treatment (e.g. methadone), and (iii) other agents (e.g. buprenorphine, clonidine) to help withdrawal from opioid drugs as a means of entry into treatment. Some opioid antagonists are not pure antagonists but in fact do produce some weak opioid partial agonist effects, and can produce analgesic effects when administered in high doses to opioid-naive individuals. Examples of such compounds include nalorphine and levallorphan. Some opioids can also have disadvantages such as worsening respiratory depression in patients who have overdosed on non-opioid sedatives such as alcohol or barbiturates.

Opioid antagonists have therapeutic potential in the treatment of a variety of disorders. These include, for instance, constipation, drug addiction, food intake, shock, alcoholism, mental and stress related disorders. The universal opioid antagonist naloxone, which is a competitive antagonist of all three types of opioid receptors (MOR, KOR and DOR), is being used to reverse the potentially lethal respiratory depression caused by neurolept analgesia or opioid overdose.

Among other pharmacological effects, it antagonizes the blood pressure drop in various forms of shock, reverses neonatal hypoxic apnea, counteracts chronic idiopathic constipation, reduces the food intake in humans and shows beneficial effects in central nervous system injuries. Its analogue naltrexone has considerable and longer duration of action higher oral efficacy, which make it suitable for the management of opioid and alcohol dependence. The opioid antagonist nalmefene (Selincro®), an analogue of naltrexone, was launched in Europe in 2013 for the reduction of alcohol consumption in alcohol dependent patients.

Several ligands, both small-molecules and peptides, interacting with the KOR have been developed over the years. The major classes of KOR agonists comprise benzomorphans (e.g. bremazocine, pentazocine), morphinans (e.g. nalfurafine), arylacetamides (e.g. U50,488, 2-(3,4-dichlorophenyl)-N-methyl-N-[(1R,2R)-2-pyrrolidin-1-ylcyclohexyl]acetamide U69,593, N-methyl-2-phenyl-N-[(5R,7S,8S)-7-(pyrrolidin-1-yl)-1-oxaspiro[4.5]dec-8-yl]acetamide), neoclerodane diterpenes (e.g. salvinorin A and analogues), and peptides (e.g. dynorphin analogues). Some notable examples of selective KOP receptor antagonists include the morphinans nor-binaltorphimine (nor-BNI) and 5'-guanidinonaltrindole (GNTI), and the structurally distinct molecule JDTic, a trans-3,4-dimethyl-4-(3-hydroxyphenyl)piperidine derivative, the latter was used to elucidate the crystal structure of the human KOP receptor. In contrast to the aforementioned KOR antagonists (nor-BNI, GNTI and JDTic) known to exhibit long-lasting pharmacokinetic properties, shorter-acting and selective KOR antagonists were developed, such as the new JDTic analogue BU09059, and the pyrrolidine derivative LY-2456302, the latter one is currently under development as an augmentation to anti-depressant therapy for treatment-resistant depression. In addition to dynorphin A analogues, arodyn (Ac[Phe$^{1,2,3}$,Arg$^4$,D-Ala$^8$]dynorphin A-(1-11) amide), zyklophin ([N-BenzylTyr$^1$,cyclo(D-Asp$^5$,Dap$^8$)]dynorphin A(1-11)-NH$_2$), and other peptides unrelated to the endogenous opioid peptide were recognized as selective KOR antagonists, for example the macrocyclic peptide cyclo[Phe-D-Pro-Phe-Trp] (CJ-15,208) and derivatives.

In the Journal of Medicinal Chemistry 2012, 55, pp. 10302-10306, six 3-hydroxy substituted diphenethylamine derivatives bearing different substituents at the nitrogen were described as KOR ligands. The N-cyclobutylmethyl substituted derivative (compound 4 in Journal of Medicinal Chemistry 2012, 55, pp. 10302-10306, referred to herein as HS665) was found to have the highest antinociceptive potency of this series.

SUMMARY OF THE INVENTION

It is an object of the invention to produce novel compounds which interact with the KOR. Surprisingly, it has now been found that e.g. N-cyclopentylmethyl, N-cyclohexylmethyl or N-benzyl substituted diphenethylamine derivatives are highly active KOR ligands, which exhibit considerably better binding affinity to the KOR and higher antinociceptive potency than their earlier published counterparts (e.g. HS665). It was also found that introduction of a second 3-hydroxy group at the other phenyl group of diphenethylamines is able to increase both, KOR binding and antinociceptive effect. It was also unexpected that a single hydroxy group at 4-position of one of the two phenyl rings of diphenethylamines gives rise to good KOR binding affinity.

It was very much surprising that other substituents than hydroxy at the phenyl ring(s) of diphenethylamines produce compounds with good KOR binding affinity.

It was particularly surprising that the new KOR partial agonists showed higher antinociceptive potency than the full KOR agonists HS665 and U50,488.

This invention provides highly active KOR compounds of the formula (I)

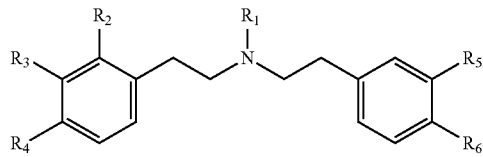

Formula (I)

in which the substituents have the following meaning:

$R_1$ is selected from $C_7$-$C_{30}$-unbranched alkyl; $C_3$-$C_{30}$-branched alkyl; $C_2$-$C_{30}$-alkenyl; $C_2$-$C_{30}$-alkynyl; $C_1$-$C_{30}$-monohydroxyalkyl; $C_2$-$C_{30}$-dihydroxyalkyl; $C_3$-$C_{30}$-trihydroxyalkyl; $C_3$-$C_{12}$-cycloalkyl; $C_4$-$C_{30}$-cycloalkylalkyl; $C_5$-$C_{30}$-cycloalkylalkenyl; $C_5$-$C_{30}$-cycloalkylalkynyl; $C_7$-$C_{30}$-arylalkyl; $C_8$-$C_{30}$-arylalkenyl; $C_8$-$C_{30}$-arylalkynyl;

$R_2$ is hydrogen, F, Cl, I, $NO_2$, CN, SH, $CO_2H$, $CONH_2$, $SO_3H$, $SO_2NH_2$, $CONHSO_3H$, $NHCONHSO_2H$, $PO_3H$, $PO_2H$, $CF_3$;

$R_3$ is hydrogen; hydroxy; OCOA, wherein A is selected from $C_1$-$C_6$-alkyl, $C_6$-$C_{14}$-aryl, $C_7$-$C_{16}$-aryalkyl; F; Cl; Br; I; $NO_2$; CN; SH; $CO_2H$; $CONH_2$; $SO_3H$; $SO_2NH_2$; $CONHSO_3H$; $NHCONHSO_2H$; $PO_3H$; $PO_2H$; $CF_3$;

$R_4$ is hydrogen; F; Cl; I; $NO_2$; CN; SH; $CO_2H$; $CONH_2$; $SO_3H$; $SO_2NH_2$; $CONHSO_3H$; $NHCONHSO_2H$; $PO_3H$; $PO_2H$; $CF_3$;

$R_5$ is hydrogen; hydroxy; $C_1$-$C_{20}$-alkoxy; OCOA, wherein A is selected from $C_1$-$C_6$-alkyl, $C_6$-$C_{14}$-aryl, $C_7$-$C_{16}$-aryalkyl;

$R_6$ is hydrogen; hydroxy; $C_1$-$C_{20}$-alkoxy; OCOA, wherein A is selected from $C_1$-$C_6$-alkyl, $C_6$-$C_{14}$-aryl, $C_7$-$C_{16}$-aryalkyl;

the nitrogen joined with $R_1$ can also be quaternized by two substituents $R_1$, which can be the same or different and which are defined as previously shown, and whereby the second, quaternized substituent can additionally have the meaning methyl, ethyl, propyl, butyl, pentyl, hexyl, hydroxy, oxyl (N oxide) as well as alkoxy;

with the proviso that $R_1$ cannot be cyclobutylmethyl (CBM) or cyclopropylmethyl (CPM) if $R_3$ is hydroxy and $R_2$, $R_4$, $R_5$ and $R_6$ is hydrogen;

if $R_3$ is hydrogen, $R_5$ and $R_6$ may not be simultaneously hydroxy; alkoxy or OCOA;

if $R_1$ is alkyl (branched or unbranched), $R_2$, $R_3$, $R_4$, $R_5$ and $R_6$ may not be simultaneously hydrogen;

and pharmaceutically acceptable acid addition salts as well as base addition salts and easily accessible derivatives (e.g. esters, ethers, amides).

Preference is given to compounds wherein $R_1$ is selected from $C_7$-$C_{12}$-unbranched alkyl; $C_3$-$C_{12}$-branched alkyl; $C_2$-$C_{12}$-alkenyl; $C_2$-$C_{12}$-alkynyl; $C_1$-$C_{12}$-monohydroxyalkyl; $C_2$-$C_{12}$-dihydroxyalkyl; $C_3$-$C_{12}$-trihydroxyalkyl; $C_3$-$C_6$-cycloalkyl; $C_4$-$C_{16}$-cycloalkylalkyl; $C_5$-$C_{16}$-cycloalkylalkenyl; $C_5$-$C_{16}$-cycloalkylalkynyl; $C_7$-$C_{16}$-arylalkyl; $C_8$-$C_{16}$-arylalkenyl; $C_8$-$C_{16}$-arylalkynyl;

$R_2$, $R_3$, $R_4$, $R_5$, and $R_6$ are as defined above.

In one embodiment, particular preference is given to compounds wherein $R_1$ is selected from $C_3$-$C_5$-branched alkyl; $C_2$-$C_6$-alkenyl; $C_2$-$C_6$-alkynyl; $C_1$-$C_6$-monohydroxyalkyl; $C_2$-$C_6$-dihydroxyalkyl; $C_3$-$C_6$-trihydroxyalkyl; $C_3$-$C_6$-cycloalkyl; $C_4$-$C_{12}$-cycloalkylalkyl, where cycloalkyl is $C_3$-$C_6$-cycloalkyl and alkyl is $C_1$-$C_6$-alkyl, preferably $C_1$-alkyl; $C_5$-$C_{12}$-cycloalkylalkenyl, where cycloalkyl is $C_3$-$C_6$-cycloalkyl and alkenyl is $C_2$-$C_6$-alkenyl, preferably $C_2$-alkenyl; $C_5$-$C_{12}$-cycloalkylalkynyl, where cycloalkyl is $C_3$-$C_6$-cycloalkyl and alkynyl is $C_2$-$C_6$-alkynyl, preferably $C_2$-alkynyl; $C_7$-$C_{12}$-arylalkyl where aryl is $C_6$-aryl and alkyl is $C_1$-$C_6$-alkyl, preferably $C_1$-alkyl; $C_8$-$C_{12}$-arylalkenyl where aryl is $C_6$-aryl and alkenyl is $C_2$-$C_6$-alkenyl, preferably $C_2$-alkenyl; $C_8$-$C_{12}$-arylalkynyl where aryl is $C_6$-aryl and alkynyl is $C_2$-$C_6$-alkynyl, preferably $C_2$-alkynyl;

$R_2$, $R_3$, $R_4$, $R_5$, and $R_6$ are as defined above. Particularly preferred are compounds as defined above, wherein $R_2$ is selected from hydrogen, F, Cl, and I; $R_3$ is selected from hydrogen and hydroxy; $R_4$ is selected from hydrogen, F, Cl, and I; $R_5$ is selected from hydrogen, hydroxy, and $C_1$-$C_6$-alkoxy; $R_6$ is selected from hydrogen, hydroxy, and $C_1$-$C_6$-alkoxy. Alternatively, particularly preferred are compounds as defined above, wherein $R_2$ is selected from hydrogen, F, Cl, and I; $R_3$ is hydroxy; $R_4$ is selected from hydrogen, F, Cl, and I; $R_5$ is selected from hydroxy and $C_1$-$C_6$-alkoxy; $R_6$ is selected from hydrogen, hydroxy, and $C_1$-$C_6$-alkoxy.

In one embodiment, particular preference is given to compounds as defined above wherein $R_1$ is selected from $C_3$-$C_6$-cycloalkyl; $C_4$-$C_{12}$-cycloalkylalkyl, where cycloalkyl is $C_3$-$C_6$-cycloalkyl and alkyl is $C_1$-$C_6$-alkyl, preferably $C_2$-alkyl; $C_5$-$C_{12}$-cycloalkylalkenyl, where cycloalkyl is $C_3$-$C_6$-cycloalkyl and alkenyl is $C_2$-$C_6$-alkenyl, preferably $C_2$-alkenyl; $C_5$-$C_{12}$-cycloalkylalkynyl, where cycloalkyl is $C_3$-$C_6$-cycloalkyl and alkynyl is $C_2$-$C_6$-alkynyl, preferably $C_2$-alkynyl; $C_7$-$C_{12}$-arylalkyl where aryl is $C_6$-aryl and alkyl is $C_1$-$C_6$-alkyl, preferably $C_1$-alkyl; $C_8$-$C_{12}$-arylalkenyl where aryl is $C_6$-aryl and alkenyl is $C_2$-$C_6$-alkyl, preferably $C_2$-alkenyl; $C_8$-$C_{12}$-arylalkynyl where aryl is $C_6$-aryl and alkynyl is $C_2$-$C_6$-alkyl, preferably $C_2$-alkynyl; and $R_2$, $R_3$, $R_4$, $R_5$, and $R_6$ are as defined above. Particularly preferred are compounds as defined above, wherein $R_2$ is selected from hydrogen, F, Cl, and I; $R_3$ is selected from hydrogen and hydroxy; $R_4$ is selected from hydrogen, F, Cl, and I; $R_5$ is selected from hydrogen, hydroxy, and $C_1$-$C_6$-alkoxy; $R_6$ is selected from hydrogen, hydroxy, and $C_1$-$C_6$-alkoxy. Alternatively, particularly preferred are compounds as defined above, wherein $R_2$ is selected from hydrogen, F, Cl, and I; $R_3$ is hydroxy; $R_4$ is selected from hydrogen, F, Cl, and I; $R_5$ is selected from hydroxy and $C_1$-$C_6$-alkoxy; $R_6$ is selected from hydrogen, hydroxy, and $C_1$-$C_6$-alkoxy.

In another embodiment, particular preference is given to compounds as defined above wherein $R_1$ is selected from $C_3$-$C_6$-cycloalkyl; $C_6$-$C_{12}$-cycloalkylalkyl, where cycloalkyl is $C_5$-$C_6$-cycloalkyl and alkyl is $C_1$-$C_6$-alkyl, preferably $C_1$-alkyl; $C_7$-$C_{12}$-cycloalkylalkenyl, where cycloalkyl is $C_5$-$C_6$-cycloalkyl and alkenyl is $C_2$-$C_6$-alkenyl, preferably $C_2$-alkenyl; $C_7$-$C_{12}$-cycloalkylalkynyl, where cycloalkyl is $C_5$-$C_6$-cycloalkyl and alkynyl is $C_2$-$C_6$-alkynyl, preferably $C_2$-alkynyl; $C_7$-$C_{12}$-arylalkyl where aryl is $C_6$-aryl and alkyl is $C_1$-$C_6$-alkyl, preferably $C_1$-alkyl; $C_8$-$C_{12}$-arylalkenyl where aryl is $C_6$-aryl and alkenyl is $C_2$-$C_6$-alkyl, preferably $C_2$-alkenyl; $C_8$-$C_{12}$-arylalkynyl where aryl is $C_6$-aryl and alkynyl is $C_2$-$C_6$-alkynyl, preferably $C_2$-alkynyl; and $R_2$, $R_3$, $R_4$, $R_5$, and $R_6$ are as defined above. Particularly preferred are compounds as defined above, wherein $R_2$ is selected from hydrogen, F, Cl, and I; $R_3$ is selected from hydrogen and hydroxy; $R_4$ is selected from hydrogen, F, Cl, and I; $R_5$ is selected from hydrogen, hydroxy, and $C_1$-$C_6$-alkoxy; $R_6$ is selected from hydrogen, hydroxy, and $C_1$-$C_6$-alkoxy. Alternatively, particularly preferred are compounds as defined above, wherein $R_2$ is selected from hydrogen, F, Cl, and I; $R_3$ is hydroxy; $R_4$ is selected from hydrogen, F, Cl, and I; $R_5$ is selected from hydroxy and $C_1$-$C_6$-alkoxy; $R_6$ is selected from hydrogen, hydroxy, and $C_1$-$C_6$-alkoxy.

Specific preference is given to compounds as defined herein wherein $R_5$ is selected from hydroxy or $C_1$-$C_6$-alkoxy and $R_6$ is selected from hydroxy or $C_1$-$C_6$-alkoxy. Alternatively, or in addition, $R_2$ and $R_4$ are independently selected from hydrogen and F.

In this invention the terms alkyl, alkenyl and alkynyl include both branched and also unbranched alkyl, alkenyl and alkynyl groups as well as mono-, di- and trihydroxy-substituted branched and unbranched alkyl, alkenyl and alkynyl groups, unless explicitly stated as branched or unbranched alkyl groups. These groups furthermore may be substituted once twice or three times with substituents selected independently from hydroxy, halogen, nitro, cyano, thiocyanato, trifluoromethyl, $C_1$-$C_3$-alkyl, $C_1$-$C_3$-alkoxy, $CO_2H$, $CONH_2$, $CO_2(C_1$-$C_3$-alkyl), $CONH(C_1$-$C_3$-alkyl), $CON(C_1$-$C_3$-alkyl)$_2$, $CO(C_1$-$C_3$-alkyl); amino; $(C_1$-$C_3$-monoalkyl)amino, $(C_1$-$C_3$-dialkyl)amino, $C_5$-$C_6$-cycloalkylamino; $(C_1$-$C_3$-alkanoyl)amido, SH, $SO_3H$, $SO_3(C_1$-$C_3$-alkyl), $SO_2(C_1$-$C_3$-alkyl), $SO(C_1$-$C_3$-alkyl), $C_1$-$C_3$-alkylthio or $C_1$-$C_3$-alkanoylthio. Further suitable substituents are cyclic groups, including carbocycles and heterocycles which may be saturated unsaturated or aromatic. Preferred examples comprise from 3 to 8 ring atoms, selected from C, N, O, and S. The term aryl defines aromatic rings comprising preferably from 5 to 18 ring atoms and the term aryl comprises furthermore carbocyclic aryl groups as well as heterocyclic aryl groups, comprising preferably from 1 to 3 heteroatoms selected from N, O and S. Aryl can be unsubstituted or mono-, di- or tri-substituted, whereby the substituents can be chosen independently from hydroxy, halogen, nitro, cyano, thiocyanato, trifluoromethyl, $C_1$-$C_3$-alkyl, $C_1$-$C_3$-alkoxy, $CO_2H$, $CONH_2$, $CO_2(C_1$-$C_3$-alkyl), $CONH(C_1$-$C_3$-alkyl), $CON(C_1$-$C_3$-alkyl)$_2$, $CO(C_1$-$C_3$-alkyl); amino; $(C_1$-$C_3$-monoalkyl)amino, $(C_1$-$C_3$-dialkyl)amino, $C_5$-$C_6$-cycloalkylamino; $(C_1$-$C_3$-alkanoyl)amido, SH, $SO_3H$, $SO_3(C_1$-$C_3$-alkyl), $SO_2(C_1$-$C_3$-alkyl), $SO(C_1$-$C_3$-alkyl), $C_1$-$C_3$-alkylthio or $C_1$-$C_3$-alkanoylthio. The aryl groups as defined above may furthermore be fused ring systems such as naphthyl or anthracenyl or the corresponding heterocyclic groups comprising from 1 to 3 heteroatoms selected from N, O, and S. The definitions listed above for alkyl, alkenyl, alkynyl and aryl are valid for all substituents of this application.

Particularly preferred compounds of this invention are selected from:

3-[2-[Allyl(phenethyl)amino]ethyl]phenol
3-[2-[(Cyclopentylmethyl)(phenethyl)amino]ethyl]phenol
3-[2-[(Cyclohexylmethyl)(phenethyl)amino]ethyl]phenol
3-[2-[Benzyl(phenethyl)amino]ethyl]phenol
3-[2-[Propargyl(phenethyl)amino]ethyl]phenol
3-[2-[Isopropyl(phenethyl)amino]ethyl]phenol
3-[2-[Isoamyl(phenethyl)amino]ethyl]phenol
3-[2-[(Cyclobutyl)(phenethyl)amino]ethyl]phenol
N-(Cyclobutylmethyl)-N-(3-methoxyphenethyl)-2-(3-methoxyphenyl)ethanamine
N-(Cyclopropylmethyl)-N-(3-methoxyphenethyl)-2-(3-methoxyphenyl)ethanamine
N-Allyl-N-(3-methoxyphenethyl)-2-(3-methoxyphenyl)ethanamine
3,3'-[2,2'-(Cyclobutylmethylazanediyl)bis(ethane-2,1-diyl)]diphenol
3,3'-[2,2'-(Cyclopropylmethylazanediyl)bis(ethane-2,1-diyl)]diphenol
3,3'-[2,2'-(Allylazanediyl)bis(ethane-2,1-diyl)]diphenol
3-[2-(3-Methoxyphenethylamino)ethyl]phenol
4-[2-(3-Methoxyphenethylamino)ethyl]phenol
3-[2-[(Cyclohexylmethyl)(3-methoxyphenethyl)amino]ethyl]phenol
3-[2-[(Isoamyl)(3-methoxyphenethyl)amino]ethyl]phenol
3-[2-[(n-Butyl)(3-methoxyphenethyl)amino]ethyl]phenol
3-[2-[(n-Pentyl)(3-methoxyphenethyl)amino]ethyl]phenol
3-[2-[(n-Hexyl)(3-methoxyphenethyl)amino]ethyl]phenol
4-[2-[(Cyclobutylmethyl)(3-methoxyphenethyl)amino]ethyl]phenol
4-[2-[(Cyclohexylmethyl)(3-methoxyphenethyl)amino]ethyl]phenol
4-[2-[Allyl(3-methoxyphenethyl)amino]ethyl]phenol
4-[2-[n-Butyl(3-methoxyphenethyl)amino]ethyl]phenol
4-[2-[(Cyclopropylmethyl)(3-methoxyphenethyl)amino]ethyl]phenol
4-[2-[(Cyclopentylmethyl)(3-methoxyphenethyl)amino]ethyl]phenol
3-[2-[(Cyclopentylmethyl)(3-methoxyphenethyl)amino]ethyl]phenol
3,3'-[2,2'-(Cyclohexylmethylazanediyl)bis(ethane-2,1-diyl)]diphenol
3,3'-[2,2'-(Isoamylazanediyl)bis(ethane-2,1-diyl)]diphenol
3,3'-[2,2'-(n-Butylazanediyl)bis(ethane-2,1-diyl)]diphenol
3,3'-[2,2'-(n-Pentylazanediyl)bis(ethane-2,1-diyl)]diphenol
3,3'-[2,2'-(n-Hexylazanediyl)bis(ethane-2,1-diyl)]diphenol 3,3'-[2,2'-(Cyclopentylmethylazanediyl)bis(ethane-2,1-diyl)]diphenol
3-[2-[(Cyclobutylmethyl)(4-hydroxyphenethyl)amino]ethyl]phenol
3-[2-[(Cyclopropylmethyl)(4-hydroxyphenethyl)amino]ethyl]phenol
3-[2-[(Cyclohexylmethyl)(4-hydroxyphenethyl)amino]ethyl]phenol
3-[2-[Allyl(4-hydroxyphenethyl)amino]ethyl]phenol
3-[2-[n-Butyl(4-hydroxyphenethyl)amino]ethyl]phenol
1-(2-Fluoro-3-methoxyphenethyl)-2-phenethylamine
N-(2-Fluoro-3-methoxyphenethyl)-2-(3-methoxyphenyl)ethanamine
N-(Cyclopropylmethyl)-N-(2-fluoro-3-methoxyphenethyl)-2-phenylethanamine
N-(Cyclobutylmethyl)-N-(2-fluoro-3-methoxyphenethyl)-2-phenylethanamine
4-[2-(2-Fluoro-3-methoxyphenethylamino)ethyl]phenol
N-(Cyclohexylmethyl)-N-(2-fluoro-3-methoxyphenethyl)-2-phenylethanamine
N-Benzyl-N-(2-fluoro-3-methoxyphenethyl)-2-phenylethanamine
N-(Cyclobutylmethyl)-N-(2-fluoro-3-methoxyphenethyl)-2-(3-methoxyphenyl)ethanamine
4-[2-[(Cyclobutylmethyl)(2-fluoro-3-methoxyphenethyl)amino]ethyl]phenol
3-[2-[(Cyclobutylmethyl)(phenethyl)amino]ethyl]-2-fluorophenol
3-[2-[(Cyclopropylmethyl)(phenethyl)amino]ethyl]-2-fluorophenol
3-[2-[(Cyclohexylmethyl)(phenethyl)amino]ethyl]-2-fluorophenol
3-[2-[(Benzyl)(phenethyl)amino]ethyl]-2-fluorophenol
3-[2-[(Cyclobutylmethyl)(3-hydroxyphenethyl)amino]ethyl]-2-fluorophenol
3-[2-[(Cyclobutylmethyl)(4-hydroxyphenethyl)amino]ethyl]-2-fluorophenol
3-[2-[(Cyclobutylmethyl)(phenethyl)amino]ethyl]benzonitrile
3-[2-[(Cyclobutylmethyl)(phenethyl)amino]ethyl]benzamide
N-(Cyclobutylmethyl)-N-phenethyl-2-phenylethanamine
N-(Cyclobutylmethyl)-N-(3-nitrophenethyl)-2-phenylethanamine
3-[2-[(Cyclobutylmethyl)(phenethyl)amino]ethyl]aniline
4-[2-[(Cyclopentylmethyl)(phenethyl)amino]ethyl]phenol
4-[2-[(Cyclobutylmethyl)(phenethyl)amino]ethyl]phenol It has now been found that the compounds of this invention represent effective opioid receptor ligands of the type of diphenethylamines and exhibit a high therapeutic effect as analgesics, diuretics, neuroprotectives, and also as anti-itch, anti-addiction, anti-inflammatory, anti-stress, anti-obesity, anti-anxiety, anti-fear, anti-phobia, anti-panic, anti-psychotic, anti-epileptic, anti-convulsant, anti-seizure, anti-autism, anti-HIV infection and anti-depressant medications.

The compounds of the invention exhibit high KOR affinity, and/or moderate or low MOR and/or DOR affinity, and/or high KOR selectivity, as determined using a common opioid receptor binding assay, which can be routinely performed by those skilled in the art. For example, opioid receptor binding assays can be performed to determine binding affinities at human opioid receptors (KOR, MOR and DOR) using membranes from Chinese hamster ovary (CHO) cells expressing one of the human opioid receptors, according to the published procedure (Journal of Medicinal Chemistry 2012, 55, pp. 10302-10306; incorporated herein by reference in its entirety). Affinity, or inhibition constant values ($K_i$) can be calculated from competition binding curves using commonly known software packages, such as the GraphPad Prism program (San Diego, Calif., USA). Specifically, a compound of the invention can exhibit an $K_i$ for KOR of less than about 20 nM, 10 nM, 5 nM, 2 nM, more preferably less than about 1 nM, less than about 0.75 nM, less than about 0.5 nM, less than about 0.25 nM, or less than about 0.1 nM. A compound of the invention can exhibit a $K_i$ for MOR of about 50 nM or more, about 100 nM or more, about 200 nM or more, about 500 nM or more, about 1 µM or more. A compound of the invention can exhibit a $K_i$ for DOR of about 50 nM or more, about 100 nM or more, more preferably about 200 nM or more, about 500 nM or more, about 1 µM or more, or about 10 µM or more.

Preferably, the compounds of the invention exhibit high potency and moderate or high efficacy in KOR-mediated G protein activation, as determined using a common KOR-mediated G protein activation assay, which can be routinely performed by those skilled in the art. For example, KOR-mediated G protein activation studies using [$^{35}$S]GTPγS binding assays can be performed to determine the in vitro pharmacological activities with membranes from CHO cells expressing human KOR, according to the published procedure (Journal of Medicinal Chemistry 2012, 55, pp. 10302-10306; incorporated herein by reference in its entirety). Concentration-response curves can be constructed, and potency ($EC_{50}$, nM) and efficacy ($E_{max}$, as % of maximum stimulation with respect to the reference KOR agonist U69,593) can be calculated from curve fitting analysis using commonly known software packages, such as the GraphPad Prism Software. Compounds producing a stimulation of ≥85% are considered to be full agonists, while compounds with stimulation between 20 and 84.9% are partial agonists, and compounds with stimulation below 20% are antagonists. Surprisingly, compounds of the invention can be partial agonists and exhibit high in vitro potency and/or in vivo potency. Specifically, in a KOR-mediated G protein activation assay, a compound of the invention can exhibit an $EC_{50}$ of less than about 100 nM, less than about 50 nM, more preferably less than about 25 nM, less than about 15 nM, less than about 10 nM, less than about 5 nM. Further, in a KOR-mediated G protein activation assay, a compound of the invention can exhibit an $E_{max}$ of between about 20% to about 100%, between about 20% to about 95%, between about 20% to about 90%, preferably between about 20% to about 85%, about 30% to about 85%, about 40% to about 85%, more preferably about 50% to about 85%.

According to current knowledge, negative side effects (i.e. sedation, dysphoria, anhedonia, motor incoordination, reduced motivation) may result from β-arrestin2-mediated signaling events (Trends in Pharmacological Sciences, 2014, 35, pp 308.316; European Journal of Pharmacology, 2015, 763, pp 184-190). Thus, it is considered that compounds biased against β-arrestin2 recruitment may be advantageous, e.g., in avoiding negative side effects. Thus, in one embodiment, compounds of the invention are biased against β-arrestin2 recruitment or exhibit a low ability to stimulate β-arrestin2 recruitment, as determined using a common β-arrestin2 recruitment assay, which can be routinely performed by those skilled in the art. For example, the ability of stimulating of β-arrestin2 recruitment upon KOR activation can be determined using the DiscoveRx PathHunter® eXpress β-arrestin assay (DiscoveRx, Fremont, Calif.), a commonly used assay to assess β-Arrestin2 translocation for 7TM-GPCRs [www.discoverx.com], using U2OS-hMOR-β-arrestin2 cells according to the manufacturer's protocol [www.discoverx.com]. Concentration-response curves can be constructed, and potency ($EC_{50}$, nM) and efficacy ($E_{max}$, as % of maximum stimulation with respect to the reference KOR agonist U69,593, tested in the same assay under the same conditions and/or using appropriate controls) can be calculated using curve fitting analysis, e.g., using commonly known software packages such as the GraphPad Prism Software. Specifically, in a β-arrestin2 recruitment assay, a compound of the invention can exhibit an $EC_{50}$ of about 25 nM or more, about 50 nM or more, about 100 nM or more, more preferably about 200 nM or more, about 500 nM or more, about 1 μM or more, or about 10 μM or more. Further, in a β-arrestin2 recruitment assay, a compound of the invention can exhibit an $E_{max}$ between about 20% to about 100%, between about 20% to about 95%, between about 20% to about 90%, preferably between about 20% to about 85%.

Preferably, compounds of the invention may exhibit a high bias toward KOR-induced G protein signaling over β-arrestin2 recruitment. For example, bias factors toward KOR-induced G protein signaling over β-arrestin2 recruitment can be calculated using an adapted procedure previously used to quantify the biased agonism of TRV130, as described in Journal of Pharmacology and Experimental Therapeutics 2013, 344, pp 708-717; incorporated herein by reference in its entirety. A bias factor of a compound can be calculated as ratio of the intrinsic relative activity: RAi (KOR-mediated G protein activation)/RAi(β-arrestin2 recruitment), where $RAi=(E_{max}ref \times EC_{50}cpd)/(E_{max}cpd \times EC_{50}ref)$, where "cpd" refers to the test compound and "ref" refers to a reference ligand, such as U69,593. Specifically, compounds of the invention can exhibit a bias factor of more than 1, more than about 10, more than about 50, more than about 100, preferably more than about 150, more than about 250, or more than about 350 compared to the reference ligand U69,593.

Preferably, compounds of the invention may exhibit high analgesic activity and/or potency in vivo. For example, relative analgesic potency can be determined in mice after subcutaneous (s.c.) administration using the acetic acid-induced writhing test, according to the described procedure (Journal of Medicinal Chemistry 2012, 55, pp. 10302-10306; incorporated herein by reference in its entirety). For instance, antinociceptive doses ($ED_{50}$) can be measured at various time points, e.g., at 30 min after s.c. administration and compared to that of the reference KOR full agonists, such as HS665 and U50,488 or the partial KOR agonist HS666. Specifically, compounds of the invention can exhibit a relative analgesic potency relative to HS665 of about 0.4 or more, about 0.6 or more, about 0.8 or more, preferably about 1 or more, 1.2 or more, 1.4 or more, 1.6 or more, 1.8 or more, 2.0 or more, 2.5 or more, 3.0 or more, 3.5 or more, 4.0 or more. Likewise, compounds of the invention can exhibit a relative analgesic potency relative to U50,488 of about 0.4 or more, about 0.6 or more, about 0.8 or more, preferably about 1 or more, 1.2 or more, 1.4 or more, 1.6 or more, 1.8 or more, 2.0 or more, 2.5 or more, 3.0 or more, 3.5 or more, 4.0 or more. Likewise, compounds of the invention can exhibit a relative analgesic potency relative to HS666 of about 0.4 or more, about 0.6 or more, about 0.8 or more, preferably about 1 or more, 1.2 or more, 1.4 or more, 1.6 or more, 1.8 or more, 2.0 or more, 2.5 or more, 3.0 or more, 3.5 or more, 4.0 or more.

The compounds of the invention are therefore effective for the treatment of pain, neuropsychiatric disorders, comorbidities of neuropsychiatric disorders (e.g. pain and depression, pain and cognitive dysfunction, pain and addiction, pain and anxiety, addiction and depressive disorders, addiction and anxiety disorders, addiction and cognitive dysfunction, depression and cognitive dysfunction), water retention (e.g. oedema), hypoxia, ischemia, autoimmune diseases and inflammatory diseases (e.g. Crohn's disease, ulcerative colitis, irritable bowel syndrome, atherosclerosis, allergies, myopathies, cancer, pancreatitis, rheumatic diseases, rheumatoid arthritis, psoriatic arthritis, osteoarthritis, fibromyalgia, systemic lupus erythematosus, multiple sclerosis), further for the treatment of functional intestinal diseases, such as abdominal pain, dyspepsia, intestinal obstruction (ileus), constipation, or irritable bowel syndrome, for the treatment of neuro-immune disorders and neurodermitis, for the treatment of mammals, in particular humans, for the treatment of drug addiction (e.g. cocaine, opiates, alcohol, amphetamines) and withdrawal of, for the treatment of other addictions, for instance behavioral addictions (e.g. gambling, computer, internet, phone, shopping, buying, food addiction), or for the treatment of dysfunction of the reward system, or for the treatment of drug-abuse-related anxiety or for the treatment of mental, neuropsychiatric or psychiatric disorders (also called mental illnesses) such as dysphoria, depression, bipolar disorders, anhedonia, stress disorders (e.g. acute stress, episodic acute stress, acute stress disorders, chronic stress, post-traumatic stress, phobias), trauma-related disorders, mood disorders, also called affective disorders (e.g. mood changes, intense and sustained sadness, melancholia, dysthymia, or despair—major depressions, bipolar disorders), seasonal affective disorders, emotion regulation disorders, cognitive or communication disorders, or anxiety spectrum disorders, or anxiety-related disorders (e.g. generalized anxiety disorders, social anxiety disorders, panic disorders, phobias, obsessive-compulsive disorder, agoraphobia), anorexia, anorexia nervosa, bulimia, bulimia nervosa, binge-eating disorder, psychotic disorders (e.g. schizophrenia, delusional disorder, paranoia), neurological disorders (e.g. trigeminal neuralgia, stroke, restless legs syndrome, paresthesia, neuropathy, narcolepsy, Huntington's disease, dyskinesia, autism spectrum disorders including Asperger syndrome, pervasive development disorder, autistic disorder, childhood disintegrative disorder, epilepsy, convulsions, seizures), substance-related disorders, for the treatment of neurodegenerative diseases such as cognitive disorders, cognitive dysfunction disorders, or dementia (e.g. Alzheimer's disease, vascular dementia, Lewy body dementia, frontotemporal dementia, amnesia) and for the treatment neuroinflammatory diseases (e.g. Parkinson's disease), neurodegenerative and neuroprogressive illnesses, or systemic inflammation diseases.

The compounds of this invention are suitable for the production of a medicament for the treatment of pain, including acute and chronic pain, on the locomotor system such as pain in the neck, back, hip, knee, shoulder or myofascial pain, treatment of complex regional pain syndromes, phantom pain, facial neuralgia, facial pain, trigeminal neuralgia, trigeminal pain, fibromyalgia, rheumatalgia, musculoskeletal pain, low back pain, cancer pain, pain from burns, pain after accidents, pain due to chronic inflammation, visceralgia, headaches such as for example tension headaches, cervical related headache or migraine, pain after central lesions such as for example with paraplegia or thalamic lesions, neuralgic pain such as zoster neuralgia, postzoster neuralgia, ischaemic pain such as angina pectoris or peripheral occlusive arterial disease, postoperative pain, neuropathic pain such as pain with diabetic neuropathy, pain after virus infections or pain after nerve lesions.

The pharmaceutical compositions according to the invention, which contain a compound of this invention and/or a pharmaceutically acceptable salt of it as active ingredient together with a pharmaceutically acceptable carrier substance or excipient, are suitable and effective for the treatment of the conditions quoted in the description.

The application according to the invention includes application as effective analgesic, anaesthetic, anxiolytic, immunomodulating, anti-tumor, anti-proliferative, anti-inflammatory, anti-rheumatic, anti-diarrhoeal, anti-constipation, anti-pruritic, anti-itch, anti-addiction, anti-stress, anti-obesity, anti-fear, anti-phobia, anti-panic, anti-psychotic, anti-epileptic, anti-convulsive, anti-seizure, anti-human immunodeficiency virus infections, anti-depressant and anti-Parkinson substances, as neuroprotective active substances and as active substances for the prevention and treatment of intestinal disorders and also for the treatment of erectile disturbances, mood disturbances, addictive disorders, memory disorders, psychotic disorders, the chronic fatigue syndrome, psychiatric disorders, neuropsychiatric disorders, neurological disorders, sleep disorders, substance use disorders, substance induced mental disorders, personality disorders, hepatic disorders, reduced urine output (oliguria, dysuria) and oedema.

The present invention also provides medicaments comprising at least one compound according to the invention for the treatment of pain, itching, pruritus, functional intestinal diseases (e.g. diarrhoea, constipation, ileus), rheumatic complaints (e.g. including rheumatoid arthritis, arthrosis, osteoarthritis, spondylosis, lumbago, musculoskeletal pain, low back pain), inflammatory diseases, neuroinflammatory disorders, acute and chronic inflammation of the small and large intestines (e.g. irritable bowel syndrome, irritable colon syndrome, colon irritabile, colitis ulcerosa, Morbus Crohn), immune disorders, CNS disorders, sleep disorders, for the treatment of drug abuse or behavioral addictions, stress-disorders, neuropsychiatric disorders, affective-disorders, emotion regulation disorders, deficit of cognitive processes, cognition-disorders, obesity, mood disorders, anxiety spectrum disorders, depression disorders, anorexia, anorexia nervosa, bulimia, bulimia nervosa, binge-eating disorder, psychiatric or mental disorders, neurodegenerative illnesses, neuroprogressive disorders, stress disorders, bipolar disorders, epilepsy, convulsions, seizures, erectile dysfunction and/or for the suppression of rejection of transplants after transplantation on mammals, particularly on humans.

In addition, it was surprisingly found that the compounds of this invention have a very strong analgesic effect. This enables a lower dosage of the medicament, which results in a lower rate of side effects and toxicity as well as a higher patient compliance to take the medicament.

The present invention also provides medicaments comprising at least one compound of the present invention as active ingredient together with pharmaceutically acceptable carrier substance(s) or excipient(s) (e.g. permeation enhancer(s), absorption enhancer(s)) in a galenic pharmaceutical formulation (e.g. immediate, controlled, extended, sustained release formulation, parenteral (intravenous, subcutaneous, intramuscular etc.), topical, transdermal, oral, transmucosal (buccal, sublingual, sublabial etc.), nasal, rectal formulation, which are suitable for the treatment of the conditions quoted in the description.

The following are examples of the practice of the invention. They are not to be construed as limiting the scope of the invention in any way.

EXAMPLES

General Procedure for the Synthesis of Compounds 1-8

A mixture of 3-[2-(phenylethylamino)ethyl]phenol (Journal of Medicinal Chemistry 2012, 55, pp. 10302-10306; 300 mg, 1.24 mmol[1]), the corresponding alkyl or allyl bromide or cyclobutyl tosylate (in case of compound 8) (1.71 mmol[1]), and $NaHCO_3$ (229 mg, 2.73 mmol[2]) is refluxed for 48 h[3] with a catalytic amount of KI in $CH_3CN$[4] (8 mL). The end of the reaction is monitored by TLC. The mixture is cooled and filtered, the filtrate is evaporated to dryness, and the crude product is purified by column chromatography[5] to give the desired products (compounds 1-9 as oils or solids). The resulting oils or solids were used as such or converted into the hydrochloride salts. The hydrochloride salts were obtained by using the following procedure: a part of the obtained oil or solid was dissolved in $Et_2O$ and treated with $HCl/Et_2O$. The precipitate was isolated[6] and recrystallized from acetone/$Et_2O$ to afford the hydrochloride salt[7].

Different modifications of this typical procedure are possible, and are commonly known to the skilled artisan, e.g.:

1) The amount can vary from 0.01 mmol to 1000 mol.
2) The amount can vary from 0.01 mmol to 10000 mol.
3) The reaction time can vary from 0 to 500 hours.
4) $CH_3CN$ can be replaced by other solvents, preferably by acetone, ethanol, methanol, isopropanol, N,N-dimethylformamide, but also by other appropriate solvents.
5) The liquid phase for column chromatography can consist of various mixtures of dichloromethane/methanol; or dichloromethane/methanol/ammonia solution; or dichloromethane/methanol/triethylamine; or other appropriate solvents and mixtures thereof.
6) Other appropriate procedures are possible to obtain the hydrochloride salt from the bases. The product can also be isolated by evaporating the reaction mixture. Or the residue can be dissolved in water and freeze dried to obtain a lyophylisate.
7) Recrystallization of the product can be performed by using many different kinds of protic solvents such as alcohols (e.g. methanol, ethanol, isopropanol etc.) and also with different kinds of aprotic solvents such as ethers (diethyl ether, diisopropyl ether etc.), or mixtures of two or more solvents, but also by other appropriate solvents.

Example 1

3-[2-[Allyl(phenethyl)amino]ethyl]phenol (Compound 1)

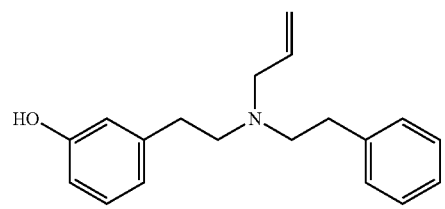

Compound 1

32% yield (oil); IR (ATR) 3193 cm$^{-1}$ (OH); $^1$H NMR (CDCl$_3$): δ 7.26-7.03 (m, 6 arom. H), 6.67-6.58 (m, 3 arom. H), 5.90-5.74 (m, 1H olefin), 5.20-5.08 (m, 2H olefin), 3.20 (d, J=7.8 Hz, $CH_2$-olefin), (2.90-2.87 (m, 8H), MS (ESI) m/z 282.25 [M+1]$^+$.

Example 2

3-[2-[(Cyclopentylmethyl)(phenethyl)amino]ethyl]phenol (Compound 2)

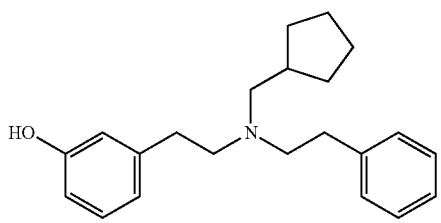
Compound 2

40% yield (transparent oil); $^1$H NMR (CDCl$_3$): δ 7.24-7.02 (m, 6 arom. H), 6.67-6.54 (m, 3 arom. H), 2.67-2.63 (m, 8H), 2.25 (d, J=7 Hz, CH$_2$-cyclopentyl), 1.69-0.73 (m, 9H).

Compound 2.HCl: white solid; Mp: 154-156° C.; IR (ATR) 3080 cm$^{-1}$ (OH); MS (ESI) m/z 323.31 [M+1]$^+$.

Example 3

3-[2-[(Cyclohexylmethyl)(phenethyl)amino]ethyl]phenol (Compound 3)

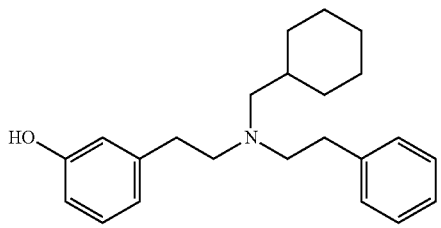
Compound 3

17% yield (yellow oil); $^1$H NMR (CDCl$_3$): δ 7.33-7.09 (m, 6 arom. H), 6.74-6.62 (m, 3 arom. H), 2.81-2.63 (m, 8H), 2.34 (d, J=7 Hz, CH$_2$-cyclohexyl), 1.77-0.81 (m, 11H).

Compound 3.HCl: beige solid; Mp: 150-151° C.; IR (ATR) 3062 cm$^{-1}$ (OH); MS (ESI) m/z 338.32 [M+1]$^+$.

Example 4

3-[2-[Benzyl(phenethyl)amino]ethyl]phenol (Compound 4)

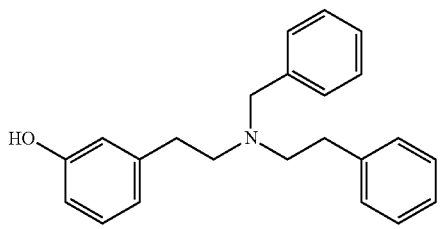
Compound 4

22% yield (yellow oil); $^1$H NMR (CDCl$_3$): δ 7.32-7.07 (m, 11 arom. H), 6.70-6.51 (m, 3 arom. H), 3.72 (s, 2H, CH$_2$-benzyl), 2.79-2.74 (m, 8H).

Compound 4.HCl: beige solid. Mp: 177-178° C.; IR (ATR) 3072 cm$^{-1}$ (OH); MS (ESI) m/z 332.26 [M+1]$^+$.

Example 5

3-[2-[Propargyl(phenethyl)amino]ethyl]phenol (Compound 5)

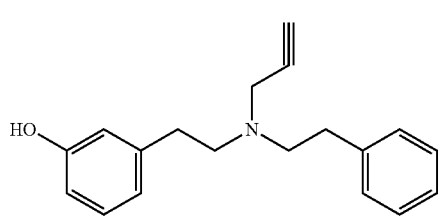
Compound 5

23% yield (yellow oil); IR (ATR) 3290 cm$^{-1}$ (C≡H), 2935 cm$^{-1}$ (OH); $^1$H NMR (CDCl$_3$): δ 7.26-7.04 (m, 6 arom. H), 6.71-6.57 (m, 3 arom. H), 3.50 (d, J=2.2 Hz, CH$_2$-propargyl), 2.74-2.70 (m, 8H), 2.16 (t, J=2.2 Hz, CH-propargyl); MS (ESI) m/z 280.41 [M+1]$^+$.

Example 6

3-[2-[Isopropyl(phenethyl)amino]ethyl]phenol (Compound 6)

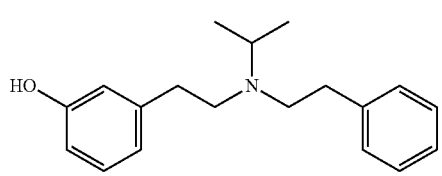
Compound 6

23% yield (beige oil); $^1$H NMR (CDCl$_3$): δ 7.39-7.09 (m, 6 arom. H), 6.74-6.66 (m, 3 arom. H), 3.16-3.03 (m, 1H, CH-isopropyl), 2.79-2.75 (m, 8H), 1.04 (d, J=6.6 Hz, (CH$_3$)$_2$-isopropyl).

Compound 6.HCl: IR (ATR) 3176 cm$^{-1}$ (OH); MS (ESI) m/z 284.14 [M+1]$^+$.

Example 7

3-[2-[Isoamyl(phenethyl)amino]ethyl]phenol (Compound 7)

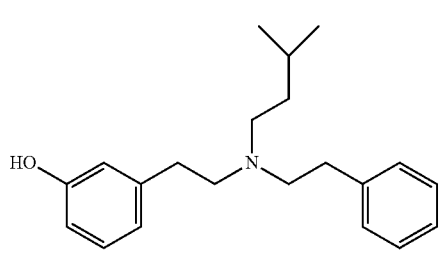
Compound 7

36% yield (yellow oil); $^1$H NMR (CDCl$_3$): δ 7.28-7.11 (m, 6 arom. H), 6.73-6.68 (m, 3 arom. H), 2.87-2.72 (m, 8H), 2.69-2.64 (m, 2H, CH$_2$-isoamyl), 1.51-1.41 (m, 3H, CH+CH$_2$-isoamyl), 0.90 (d, J=6.6 Hz, (CH$_3$)$_2$-isoamyl).

Compound 7.HCl: yellow solid; Mp: 149-150° C.; IR (ATR) 3095 cm$^{-1}$ (OH); MS (ESI) m/z 312.26 [M+1]$^+$.

Example 8

3-[2-[Cyclobutyl(phenethyl)amino]ethyl]phenol (Compound 8)

Compound 8

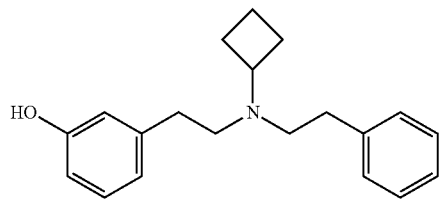

32% yield (yellow oil); $^1$H NMR (CDCl$_3$): δ 7.21-7.07 (m, 6 arom. H), 6.65-6.60 (m, 3 arom. H), 2.90-2.71 (m, 8H), 2.51 (d, J=6.6 Hz, CH-cyclobutyl), 0.88-0.78 (m, 2H), 0.49-0.43 (m, 2H), 0.12-0.07 (m, 2H).

Compound 8.HCl: light brown solid; Mp: 100-101° C.; IR (ATR) 3161 cm$^{-1}$ (OH); MS (ESI) m/z 296.16 [M+1]$^+$.

General Procedure for the Synthesis of Compounds 9-11

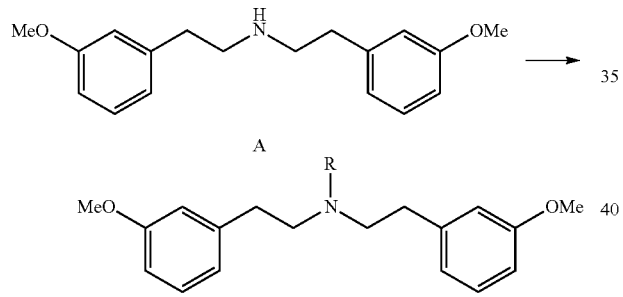

9 R = CBM
10 R = CPM
11 R = allyl

CBM = cyclobutylmethyl
CPM = cyclopropylmethyl

A mixture of N-(3-methoxyphenethyl)-2-(3-methoxyphenyl)ethanamine (A) (European Journal of Medicinal Chemistry—Chimica Therapeutica 1978, 13, pp. 553-563) (500 mg, 1.75 mmol$^1$), the corresponding alkyl or allyl bromide (1.2 mmol$^1$), and K$_2$CO$_3$ (484 mg, 3.5 mmol$^2$) in anhydrous DMF$^3$ (9 mL) is stirred under N$_2$ at 80° C.$^4$ for 14 h$^5$. 15 mL of H$_2$O are added and the aqueous phase is extracted with CH$_2$Cl$_2$ (3×20 mL), washed with brine (15 mL), dried over Na$_2$SO$_4$ and evaporated. The resulting brown oil is purified by column chromatography$^6$ to give the desired products.

Different modifications of this typical procedure are possible, and are commonly known to the skilled artisan, e.g.:
1) The amount can vary from 0.01 mmol to 1000 mol.
2) The amount can vary from 0.01 mmol to 10000 mol.
3) DMF (N,N-dimethylformamide) can be replaced by other solvents, preferably by acetone, ethanol, methanol, isopropanol, acetonitrile but also by other appropriate solvents.
4) The reaction temperature can vary from 0° C. to 160° C.
5) The reaction time can vary from 0 to 500 hours.
6) The liquid phase for column chromatography can consist of various mixtures of dichloromethane/methanol; or dichloromethane/methanol/ammonia solution; or dichloromethane/methanol/triethylamine; or other appropriate solvents and mixtures thereof.

Example 9

N-(Cyclobutylmethyl)-N-(3-methoxyphenethyl)-2-(3-methoxyphenyl)ethanamine (Compound 9)

Compound 9

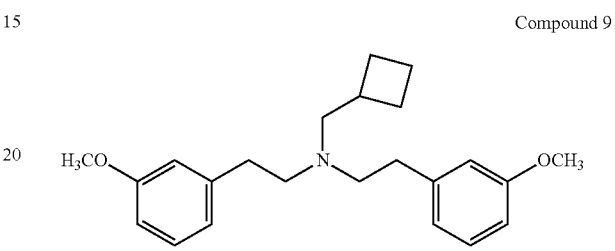

40% yield (yellow oil); $^1$H NMR (CDCl$_3$): δ 23-7.15 (m, 2 arom. H), 6.79-6.75 (m, 6 arom. H), 3.79 (s, 2×CH$_3$O), 2.95-2.71 (m, 8H), 2.62-2.53 (m, 2H), 2.04-1.69 (m, 7H).

Example 10

N-(Cyclopropylmethyl)-N-(3-methoxyphenethyl)-2-(3-methoxyphenyl)ethanamine (Compound 10)

Compound 10

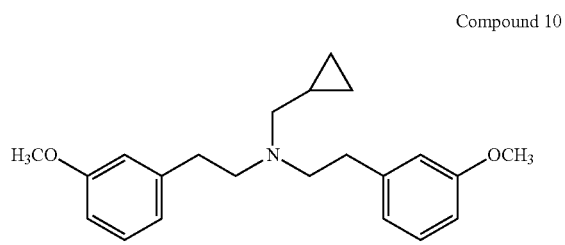 [SMILES: COc1cccc(CCN(CCc2cccc(OC)c2)CC2CC2)c1]

43% yield (yellow oil); $^1$H NMR (CDCl$_3$): δ 7.47-7.43 (m, 2 arom. H), 7.07-7.00 (m, 6 arom. H), 4.06 (s, 2×CH$_3$O), 2.95-2.71 (m, 10H), 1.18-1.15 (m, cycloprop), 0.82-0.76 (m, cycloprop), 0.47-0.42 (m, cycloprop.).

Example 11

N-Allyl-N-(3-methoxyphenethyl)-2-(3-methoxyphenyl)ethanamine (Compound 11)

Compound 11

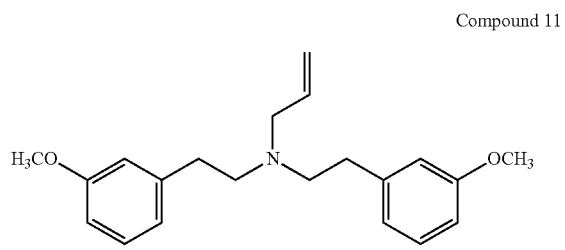 [SMILES: C=CCN(CCc1cccc(OC)c1)CCc1cccc(OC)c1]

38% yield (yellow oil); $^1$H NMR (CDCl$_3$): δ 7.24-7.15 (m, 2 arom. H), 6.79-6.60 (m, 6 arom. H), 5.94-5.82 (m, 1H olefin), 5.33-5.12 (m, 2H olefin), 4.06 (s, 2×CH$_3$O), 3.26-3.17 (m, CH$_2$-olefin), 2.95-2.71 (m, 8H).

General Procedure for the Synthesis of Compounds 12-14

A mixture of compound 9, 10 or 11 (0.7 mmol[1]) and sodium ethanethiolate[2] (942 mg, 11.2 mmol[1]) in anhydrous DMF[3] (4 mL) is stirred under N$_2$ at 130° C.[4] for 20 h[5]. After cooling, the resulting mixture is poured on saturated NH$_4$Cl solution. The resulting mixture is slightly acidified with 2N HCl and then alkalinized with diluted NH$_4$OH$_{conc.}$ solution and extracted with CH$_2$Cl$_2$ (3×15 mL). The organic phase is washed with H$_2$O (5×15 mL), brine (15 mL), dried over Na$_2$SO$_4$ and evaporated. The resulting oils are purified by column chromatography[6] to give the desired products (compounds 13-15 as oils). The resulting oils are converted into the hydrochloride salts. The hydrochloride salts are obtained by using the following procedure: A part of the obtained oil or solid is dissolved in Et$_2$O and treated with HCl/Et$_2$O[7]. The precipitate is isolated and recrystallized from acetone/Et$_2$O[8] to afford the hydrochloride salt.

Different modifications of this typical procedure are possible, and are commonly known to the skilled artisan, e.g.:
1) The amount can vary from 0.01 mmol to 1000 mol.
2) Other reagents and procedures can be used for the ether cleavage step. For instance BBr$_3$ in dichlomethane at different temperatures, aqueous hydrohalic acids or potassium hydroxide at elevated temperatures, but also other appropriate reagents and procedures.
3) DMF can be replaced by other appropriate solvents.
4) The reaction temperature can vary from −80° C. to 160° C.
5) The reaction time can vary from 0 to 500 hours.
6) The liquid phase for column chromatography can consist of various mixtures of dichloromethane/methanol; or dichloromethane/methanol/ammonia solution; or dichloromethane/methanol/triethylamine; or other appropriate solvents and mixtures thereof.
7) Other appropriate procedures are possible to obtain the hydrochloride salt from the bases. The product can also be isolated by evaporating the reaction mixture. Or the residue can be dissolved in water and freeze dried to obtain a lyophylisate.
8) Recrystallization of the product can be performed by using many different kinds of protic solvents such as alcohols (e.g. methanol, ethanol, isopropanol etc.) and also with different kinds of aprotic solvents such as ethers (diethyl ether, diisopropyl ether etc.), or mixtures of two or more solvents, but also by other appropriate solvents.

Example 12

3,3'-[2,2'-(Cyclobutylmethylazanediyl)bis(ethane-2,1-diyl)]diphenol (Compound 12)

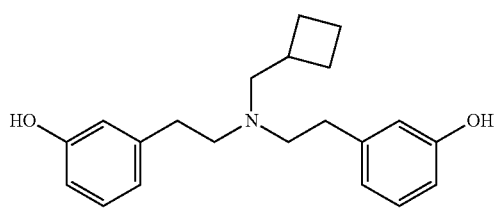

Compound 12

44% yield (transparent oil); $^1$H NMR (CDCl$_3$): δ 7.14 (t, J=8 Hz, 2 arom. H), 6.71-6.64 (m, 6 arom. H), 2.74-2.64 (m, 10H), 2.06-1.69 (m, 7H).

Compound 12.HCl: beige solid; Mp: 100-101° C.; IR (ATR) 3202 cm$^{-1}$ (OH); MS (ESI) m/z 326.27 [M+1]$^+$.

Example 13

3,3'-[2,2'-(Cyclopropylmethylazanediyl)bis(ethane-2,1-diyl)]diphenol (Compound 13)

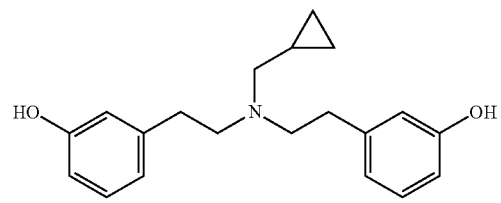

Compound 13

44% yield (yellow oil); $^1$H NMR (CDCl$_3$): δ 7.12 (t, J=8 Hz, 2 arom. H), 6.70-6.66 (m, 6 arom. H), 2.96-2.89 (m, 4H), 2.80-2.71 (m, 4H), 2.56 (d, J=6.6 Hz, CH$_2$-cycloprop), 0.92-0.90 (m, cycloprop), 0.57-0.48 (m, cycloprop), 0.19-0.12 (m, cycloprop.).

Compound 13.HCl: beige solid; Mp: 106-107° C.; IR (ATR) 3190 cm$^{-1}$ (OH); MS (ESI) m/z 312.23 [M+1]$^+$.

Example 14

3,3'-[2,2'-(Allylazanediyl)bis(ethane-2,1-diyl)]diphenol (Compound 14)

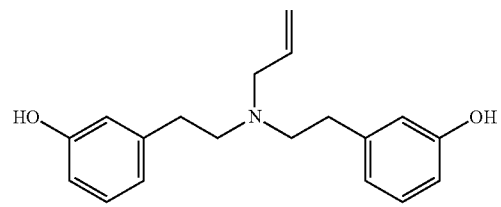

Compound 14

38% yield (yellow oil); $^1$H NMR (CDCl$_3$): δ 7.12 (t, J=8 Hz, 2 arom. H), 6.69-6.63 (m, 6 arom. H), 6.01-5.81 (m, 1H olefin), 5.27-5.16 (m, 2H olefin), 3.28 (d, J=6.6 Hz, CH$_2$-olefin), 2.78-2.76 (m, 8H).

Compound 14.HCl: beige solid. Mp: 104-106° C.; IR (ATR) 3197 cm$^{-1}$ (OH); MS (ESI) m/z 298.17 [M+1]$^+$.

General Procedure for the Synthesis of Compounds 15 and 16

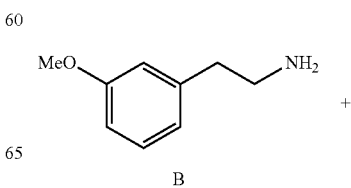

B

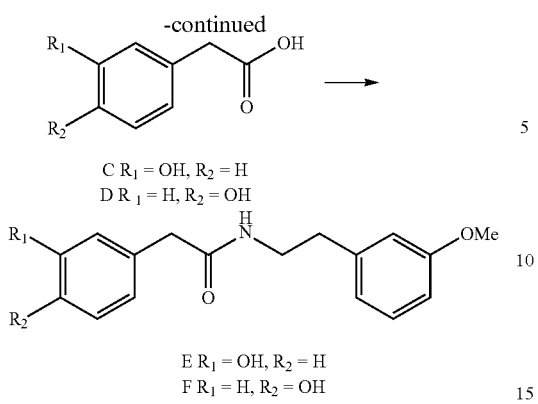

C R$_1$ = OH, R$_2$ = H
D R$_1$ = H, R$_2$ = OH

E R$_1$ = OH, R$_2$ = H
F R$_1$ = H, R$_2$ = OH

To the stirred solution of 3-hydroxyphenylacetic acid (C) or 4-hydroxyphenylacetic acid (D) (5 g, 32.85 mmol[1]), 1-(3-dimethylaminopropyl)-3-ethylcarbodiimide (EDCl)[2] (8.2 g, 42.7 mmol[2]) and 1-hydroxy-1H-benzotriazole (HOAt)[3] (6 mL, 42.7 mmol[2]) in anhydrous $CH_2Cl_2$[4] (200 mL), 3-methoxyphenethylamine (B) (5.8 mL, 39.5 mmol[2]) is added under $N_2$ at room temperature[5]. The mixture is stirred overnight[6] and then diluted to 350 mL with $CH_2Cl_2$. The organic layer is washed with $NaHCO_3$ sat. (2×100 mL), HCl 0.1 N (2×100 mL), dried over $Na_2SO_4$ and evaporated. The resulting oils are purified by column chromatography[6] to give the intermediates 2-(3-hydroxyphenyl)-N-(3-methoxyphenethyl)acetamide (E): $^1$H NMR (CDCl$_3$) δ 7.29-6.95 (m, 2 arom. H), 6.84-6.63 (m, 6 arom. H), 6.01 (br, s, $^+$NH), 3.73 (s, CH$_3$O), 3.47-3.37 (m, 2H), 2.92 (s, 1H), 2.85 (s, 1H), 2.72 (t, J=6.6 Hz, 2H), and 2-(4-hydroxyphenyl)-N-(3-methoxyphenethyl)acetamide (F): $^1$H NMR (CDCl$_3$) δ 7.16 (t, J=8.2 Hz, 2 arom. H), 7.03 (d, J=8. Hz, 2 arom. H), 6.80-6.72 (m, 2 arom. H), 6.63-6.61 (m, 2 arom. H), 5.48 (br, s, $^+$NH), 3.77 (s, CH$_3$O), 3.42-3.47 (m, 2H), 2.97 (s, 1H), 2.89 (s, 1H), 2.70 (t, J=6.6 Hz, 2H) as transparent oils.

To a solution of 2-(3-hydroxyphenyl)-N-(3-methoxyphenethyl)acetamide (E) or 2-(4-hydroxyphenyl)-N-(3-methoxyphenethyl)acetamide (F) (5 g, 17.5 mmol[1]) in anhydrous THF (150 mL) is added $BH_3$.THF 1M (87.5 mL, 87.5 mmol[1]) under $N_2$ at 0° C.[5]. The reaction mixture is refluxed overnight[6] and then, after cooling, MeOH is added to destroy the excess of $BH_3$. The solvent is evaporated, $H_2O$ (200 mL) and NaOH 0.1 N (50 mL) are added. The aqueous phase is extracted with $CH_2Cl_2$ (3×20 mL), washed with $H_2O$ (3×100 mL) and brine (100 mL), dried over $Na_2SO_4$ and evaporated. The resulting oils are purified by column chromatography[7] to give the desired products (compounds 15 and 16) as transparent oils.

Different modifications of this typical procedure are possible, and are commonly known to the skilled artisan, e.g.:

1) The amount can vary from 0.01 mmol to 1000 mol.
2) Instead of EDCl also other carbodiimides such as N,N'-dicyclohexylcarbodiimide (DCC), N,N'-diisopropylcarbodiimide or other coupling reagents can be used.
3) 1-Hydroxy-7-azabenzotriazol (HOAt) is a coupling reagent which can be substituted by hydroxybenzotriazol (HOBT), 6-chloro-1-hydroxybenzotriazole (Cl-HOBt), (1-[Bis(dimethylamino)methylene]-1H-1,2,3-triazolo[4,5-b]pyridinium-3-oxid hexafluorophosphate) (HATU), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), 3-hydroxy-3,4-dihydro-4-oxo-1,2,3-benzotriazole, N-hydroxy-5-norbornene-2,3-dicarboximide (HONB), N-hydroxysuccinimide or ethyl-2-cyano-2-(hydroxyimino)acetat and others.
4) Other solvents such as tetrahydrofurane, acetonitrile N,N-dimethylformamide or others can be used.
5) The reaction temperature can vary from −80° C. to 160° C.
6) The reaction time can vary from 0 to 500 hours.
7) The liquid phase for column chromatography can consist of various mixtures of dichloromethane/methanol; or dichloromethane/methanol/ammonia solution; or dichloromethane/methanol/triethylamine; or other appropriate solvents and mixtures thereof.

Example 15

3-[2-(3-Methoxyphenethylamino)ethyl]phenol (Compound 15)

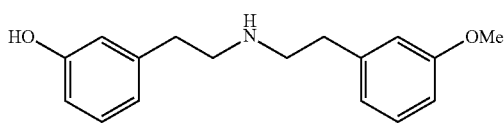

Compound 15

64% yield (transparent oil); $^1$H NMR (CDCl$_3$): δ 7.17-7.06 (m, 2 arom. H), 6.79-6.49 (m, 6 arom. H), 3.79 (s, CH$_3$O), 3.06-2.74 (m, 8H).

Example 16

4-[2-(3-Methoxyphenethylamino)ethyl]phenol (Compound 16)

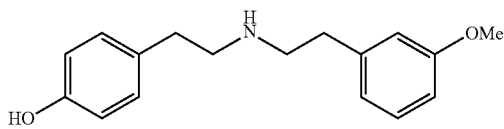

Compound 16

70% yield (transparent oil); $^1$H NMR (CDCl$_3$): δ 7.16 (t, J=8 Hz, 2 arom. H), 7.01-6.88 (m, 2 arom. H), 6.78-6.62 (m, 4 arom. H), 3.77 (s, CH$_3$O), 3.04-2.78 (m, 8H).

General Procedure for the Synthesis of Compounds 17-28

A mixture of compound 15 or 16 (500 mg, 1.8 mmol[1]), the corresponding alkyl or allyl bromide (2.6 mmol[1]), and $NaHCO_3$ (322 mg, 3.96 mmol[2]) is refluxed for 48 h[3] with a catalytic amount of KI in $CH_3CN$[4] (5 mL). The mixture is cooled and filtered, the filtrate is evaporated to dryness, and the crude product is purified by column chromatography[5] to give the desired products as oils (compounds 17-27).

Different modifications of this typical procedure are possible, and are commonly known to the skilled artisan, e.g.:

1) The amount can vary from 0.01 mmol to 1000 mol.
2) The amount can vary from 0.01 mmol to 10000 mol.
3) The reaction time can vary from 0 to 500 hours.

4) CH$_3$CN can be replaced by other solvents, preferably by acetone, ethanol, methanol, isopropanol, N,N-dimethylformamide, but also by other appropriate solvents.
5) The liquid phase for column chromatography can consist of various mixtures of dichloromethane/methanol; or dichloromethane/methanol/ammonia solution; or dichloromethane/methanol/triethylamine; or other appropriate solvents and mixtures thereof.

Example 17

3-[2-[(Cyclohexylmethyl)(3-methoxyphenethyl)amino]ethyl]phenol (Compound 17)

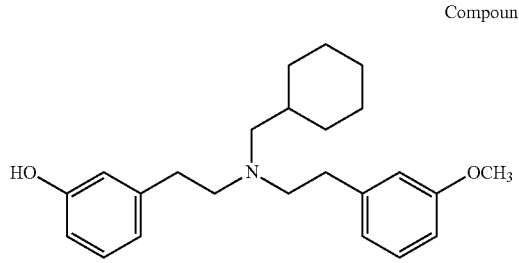

Compound 17

43% yield (yellow oil); $^1$H NMR (CDCl$_3$): δ 7.20-7.04 (m, 2 arom. H), 6.72-6.56 (m, 6 arom. H), 3.77 (s, CH$_3$O), 2.95-2.63 (m, 8H), 2.1 (d, J=7 Hz, CH$_2$-cyclohexyl), 1.88-0.96 (m, 11H).

Example 18

3-[2-[Isoamyl(3-methoxyphenethyl)amino]ethyl]phenol (Compound 18)

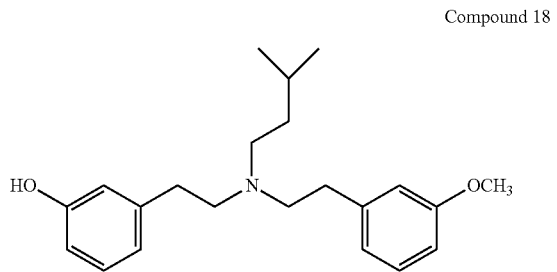 [SMILES: COc1cccc(CCN(CCc2cccc(O)c2)CCC(C)C)c1]

Compound 18

61% yield (yellow oil); $^1$H NMR (CDCl$_3$): δ 7.16-7.10 (m, 2 arom. H), 6.82-6.67 (m, 6 arom. H), 3.79 (s, CH$_3$O), 2.94-2.77 (m, 8H), 2.65-2.58 (m, 2H, CH$_2$-isoamyl), 1.39-1.34 (m, 3H, CH+CH$_2$-isoamyl), 0.90 (d, J=6.2 Hz, (CH$_3$)$_2$-isoamyl).

Example 19

3-[2-[n-Butyl(3-methoxyphenethyl)amino]ethyl]phenol (Compound 19)

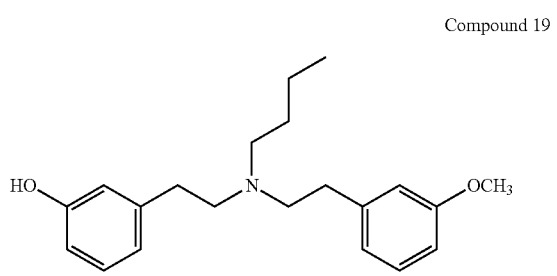 [SMILES: CCCCN(CCc1cccc(O)c1)CCc1cccc(OC)c1]

Compound 19

31% yield (yellow oil); $^1$H NMR (CDCl$_3$): δ 7.25-7.10 (m, 2 arom. H), 6.88-6.70 (m, 6 arom. H), 3.80 (s, CH$_3$O), 3.75-3.58 (m, 2H, CH$_2$—N), 3.18-3.00 (m, 8H), 1.50-1.25 (m, 4H, 2×CH$_2$-butyl), 1.03-0.88 (m, 3H, CH$_3$-butyl).

Example 20

3-[2-[n-Pentyl(3-methoxyphenethyl)amino]ethyl]phenol (Compound 20)

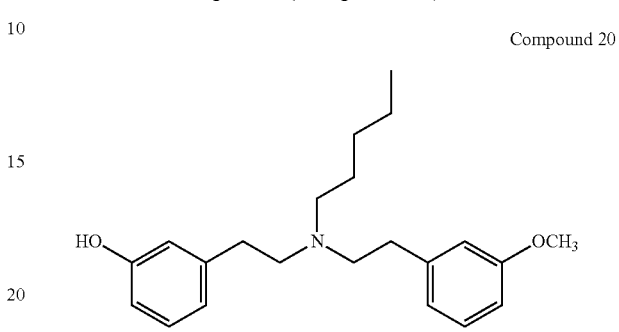

Compound 20

27% yield (yellow oil); $^1$H NMR (CDCl$_3$): δ 7.25-7.08 (m, 2 arom. H), 6.83-6.66 (m, 6 arom. H), 3.79 (s, CH$_3$O), 3.19-2.96 (m, 10H, CH$_2$—N+8H), 1.28 (br, s, 6H, 3×CH$_2$-pentyl), 0.88-0.85 (m, 3H, CH$_3$-pentyl).

Example 21

3-[2-[n-Hexyl(3-methoxyphenethyl)amino]ethyl]phenol (Compound 21)

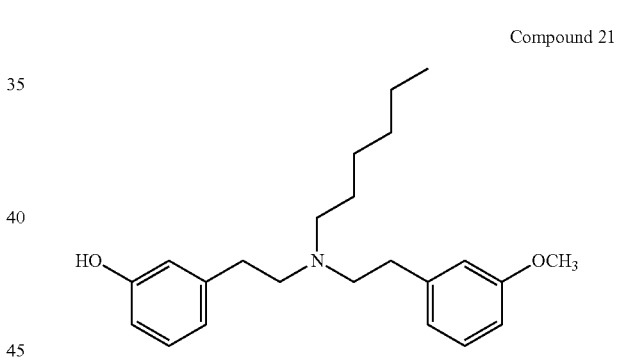

Compound 21

33% yield (yellow oil); $^1$H NMR (CDCl$_3$): δ 7.25-7.09 (m, 2 arom. H), 6.90-6.69 (m, 6 arom. H), 3.80 (s, CH$_3$O), 3.63-3.46 (m, 2H, CH$_2$—N), 3.20-3.00 (m, 8H), 1.32-1.25 (m, 8H, 4×CH$_2$-hexyl), 0.90-0.88 (m, 3H, CH$_3$-hexyl).

Example 22

4-[2-[(Cyclobutylmethyl)(3-methoxyphenethyl)amino]ethyl]phenol (Compound 22)

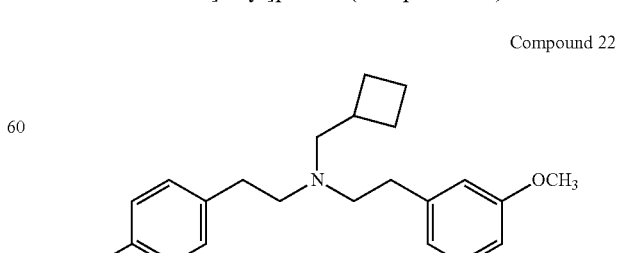

Compound 22

57% yield (yellow oil); ¹H NMR (CDCl₃): δ 7.19 (t, J=7.8 Hz, 2 arom. H), 7.04-7.00 (m, 2 arom. H), 6.77-6.73 (m, 4 arom. H), 3.79 (s, CH₃O), 2.75-2.59 (m, 10H), 2.08-1.7 (m, 7H).

Example 23

4-[2-[(Cyclohexylmethyl)(3-methoxyphenethyl)amino]ethyl]phenol (Compound 23)

Compound 23

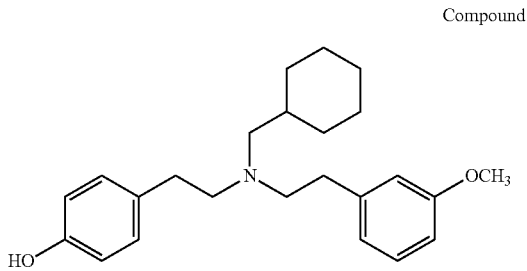

45% yield (yellow oil); ¹H NMR (CDCl₃): δ 7.19 (t, J=7.4 Hz, 2 arom. H), 7.03 (d, J=8.4 Hz 2 arom. H), 6.79-6.72 (m, 4 arom. H), 3.8 (s, CH₃O), 2.71-2.76 (m, 10H), 2.3 (d, J=7 Hz, CH₂-cyclohexyl), 1.43-0.85 (m, 11H).

Example 24

4-[2-[Allyl(3-methoxyphenethyl)amino]ethyl]phenol (Compound 24)

Compound 24

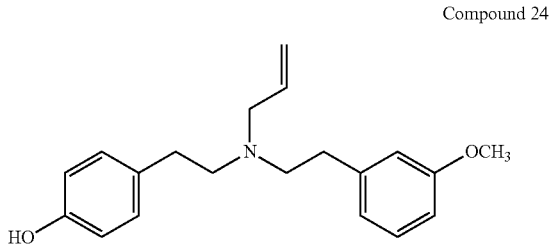 [SMILES: C=CCN(CCc1ccc(O)cc1)CCc1cccc(OC)c1]

33% yield (yellow oil); ¹H NMR (CDCl₃): δ 7.22-7.16 (m, 2 arom. H), 7.03 (d, J=8.4 Hz 2 arom. H), 6.78-6.74 (m, 4 arom. H), 5.98-5.79 (m, 1H olefin), 5.30-5.28 (m, 2H olefin), 3.80 (s, CH₃O), 3.28 (d, J=6.4 Hz, CH₂-olefin), 2.80-2.75 (m, 8H).

Example 25

4-[2-[n-Butyl(3-methoxyphenethyl)amino]ethyl]phenol (Compound 25)

Compound 25

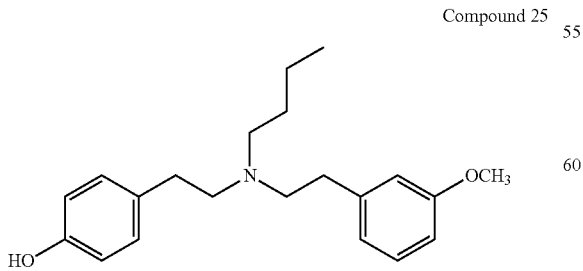

30% yield (yellow oil); ¹H NMR (CDCl₃): δ 7.26-7.17 (m, 2 arom. H), 7.01-6.96 (m, 2 arom. H), 6.85-6.76 (m, 4 arom. H), 3.79 (s, CH₃O), 3.12-2.88 (m, 10H), 1.69-1.61 (m, 2H, CH₂-butyl), 1.40-1.25 (m, 2H, CH₂-butyl), 0.97-0.90 (m, 3H, CH₃-butyl).

Example 26

4-[2-[(Cyclopropylmethyl)(3-methoxyphenethyl)amino]ethyl]phenol (Compound 26)

Compound 26

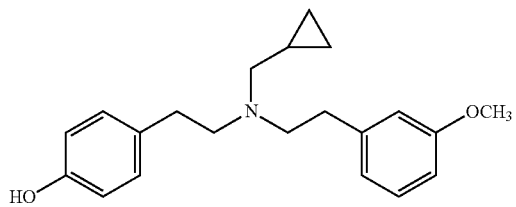

39% yield (yellow oil); ¹H NMR (CDCl₃): δ 7.22 (t, J=8.8 Hz, 2 arom. H), 7.04-7.01 (m, 2 arom. H), 6.80-6.75 (m, 4 arom. H), 3.80 (s, CH₃O), 3.11-2.80 (m, 8H), 2.71 (d, J=6.2 Hz, CH₂-cyclopropyl), 1.03-0.58 (m, 4H), 0.31-0.24 (m, 1H).

Example 27

4-[2-[(Cyclopentylmethyl)(3-methoxyphenethyl)amino]ethyl]phenol (Compound 27)

Compound 27

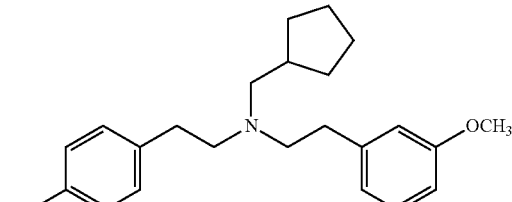

60 mg, 23% yield (yellow oil); ¹H NMR (CDCl₃): δ 7.24-7.16 (m, 1 arom. H), 7.06-7.02 (m, 2 arom. H), 6.79-6.73 (m, 5 arom. H), 3.80 (s, CH₃O), 2.79-2.74 (m, 8H), 2.54-2.51 (m, 2H, CH₂-cyclopentylmethyl), 2.12-2.05 (m, 1H), 1.73-1.19 (m, 8H).

A part of the obtained oil of compound 27 was dissolved in Et₂O and treated with HCl/Et₂O. The precipitate was isolated and recrystallized from acetone/Et₂O to afford 27.HCl as beige solid; Mp: 74-77° C.; IR (ATR) 3139 cm⁻¹ (OH); MS (ESI) m/z 354.5 [M+1]⁺.

Example 28

3-[2-[(Cyclopentylmethyl)(3-methoxyphenethyl)amino]ethyl]phenol (Compound 28)

Compound 28

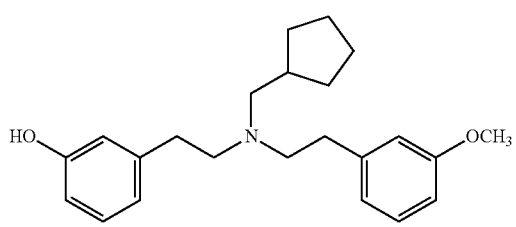

65 mg, 25% yield (yellow oil); ¹H NMR (CDCl₃): δ 7.24-7.10 (m, 3 arom. H), 6.81-6.68 (m, 5 arom. H), 3.81 (s, CH₃O), 2.88 (br, s, 8H), 2.66-2.62 (m, CH₂-cyclopentyl), 2.18-2.09 (m, 1H), 1.60-1.25 (m, 8H).

General Procedure for the Synthesis of Compounds 29-38

A mixture of starting material (compound 18, 19, 20, 21, 22, 23, 24, 25, 26 or 27) (1.03 mmol[1]) and sodium ethanethiolate[2] (550 mg, 6.53 mmol[1]) in anhydrous DMF[3] (5 mL) was stirred under N₂ at 130° C.[4] (bath temperature) for 20 h[5]. After cooling, the mixture was poured on saturated NH₄Cl solution. The resulting mixture was slightly acidified with 2N HCl and then alkalinized with diluted NH₄OH$_{conc.}$ solution and extracted with CH₂Cl₂ (3×15 mL). The organic phase was washed with H₂O (5×15 mL), brine (15 mL), dried over Na₂SO₄ and evaporated. The resulting oils were purified by column chromatography[6] to give the desired compounds as transparent oils (compounds 13-15). The resulting oils are converted into the hydrochloride salts. The hydrochloride salts are obtained by using the following procedure: A part of the obtained oil or solid is dissolved in Et₂O and treated with HCl/Et₂O[7]. The precipitate is isolated and recrystallized from acetone/Et₂O[8] to afford the hydrochloride salt.

Different modifications of this typical procedure are possible, and are commonly known to the skilled artisan, e.g.:
1) The amount can vary from 0.01 mmol to 1000 mol.
2) Other reagents and procedures can be used for the ether cleavage step. For instance BBr₃ in dichlomethane at different temperatures, aqueous hydrohalic acids or potassium hydroxide at elevated temperatures, but also other appropriate reagents and procedures.
3) DMF can be replaced by other appropriate solvents.
4) The reaction temperature can vary from −80° C. to 160° C.
5) The reaction time can vary from 0 to 500 hours.
6) The liquid phase for column chromatography can consist of various mixtures of dichloromethane/methanol; or dichloromethane/methanol/ammonia solution; or dichloromethane/methanol/triethylamine; or other appropriate solvents and mixtures thereof.
7) Other appropriate procedures are possible to obtain the hydrochloride salt from the bases. The product can also be isolated by evaporating the reaction mixture. Or the residue can be dissolved in water and freeze dried to obtain a lyophilisate.
8) Recrystallization of the product can be performed by using many different kinds of protic solvents such as alcohols (e.g. methanol, ethanol, isopropanol etc.) and also with different kinds of aprotic solvents such as ethers (diethyl ether, diisopropyl ether etc.), or mixtures of two or more solvents, but also by other appropriate solvents.

Example 29

3,3'-[2,2'-(Cyclohexylmethylazanediyl)bis(ethane-2,1-diyl)]diphenol (Compound 29)

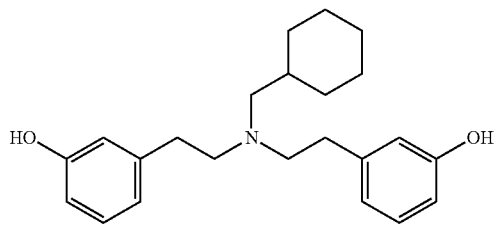

Compound 29

20% yield; ¹H NMR (CDCl₃): δ 7.03-6.96 (m, 2 arom. H), 6.60-6.48 (m, 6 arom. H), 2.54 (br, s, 8H), 2.16 (d, J=6.6 Hz, CH₂-cyclohexyl), 1.59-0.65 (m, 11H).

Compound 29.HCl: white solid; Mp: 157-158° C.; IR (ATR) 2921 cm⁻¹ (OH); MS (ESI) m/z 354.4 [M+1]⁺.

Example 30

3,3'-[2,2'-(Isoamylazanediyl)bis(ethane-2,1-diyl)]diphenol (Compound 30)

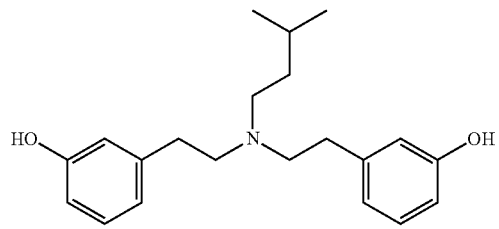

Compound 30

25% yield; ¹H NMR (CDCl₃): δ 7.15-7.07 (m, 2 arom. H), 6.69-6.63 (m, 6 arom. H), 2.76-2.60 (m, 10H),), 1.44-1.24 (m, 3H, CH+CH₂-isoamyl), 0.86 (d, J=6.2 Hz, (CH₃)₂-isoamyl).

Compound 30.HCl: yellow solid; Mp: 71-72° C.; IR (ATR) 3191 cm⁻¹ (OH); MS (ESI) m/z 328.4 [M+1]⁺.

Example 31

3,3'-[2,2'-(n-Butylazanediyl)bis(ethane-2,1-diyl)]diphenol (Compound 31)

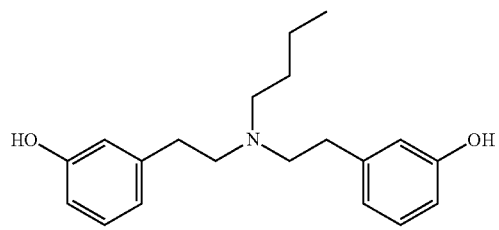

Compound 31

22% yield; ¹H NMR (CDCl₃): δ 7.33-6.90 (m, 4 arom. H), 6.73-6.65 (m, 4 arom. H), 3.44-3.35 (m, 8H), 3.01-2.93 (m, 2H, CH₂—N), 1.66-1.31 (m, 4H, 2×CH₂-butyl), 0.99-0.89 (m, 3H, CH₃-butyl).

Compound 31.HCl: slightly brown solid; Mp: 62-64° C.; IR (ATR) 3156 cm⁻¹ (OH); MS (ESI) m/z 314.3 [M+1]⁺.

Example 32

3,3'-[2,2'-(n-Pentylazanediyl)bis(ethane-2,1-diyl)]diphenol (Compound 32)

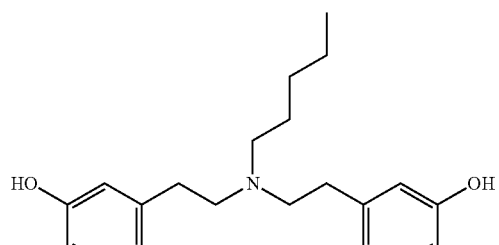

Compound 32

25% yield; $^1$H NMR (CDCl$_3$): δ 7.19-6.94 (m, 4 arom. H), 6.72 (br, s, 4 arom. H), 3.50-3.45 (m, 8H), 3.01-2.93 (m, 2H, CH$_2$—N), 1.66-1.24 (m, 6H, 3×CH$_2$-pentyl), 0.91 (t, J=5.4 Hz, 3H, CH$_3$-pentyl).

Compound 32.HCl: yellowish solid; Mp: 70-72° C.; IR (ATR) 3191 cm$^{-1}$ (OH); MS (ESI) m/z 328.4 [M+1]$^+$.

Example 33

3,3'-[2,2'-(n-Hexylazanediyl)bis(ethane-2,1-diyl)]diphenol (Compound 33)

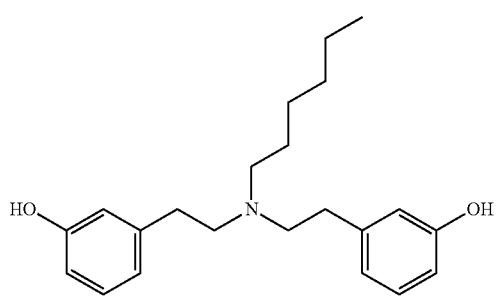

Compound 33

21% yield; $^1$H NMR (CDCl$_3$): δ 7.15-6.85 (m, 4 arom. H), 6.71-6.64 (m, 4 arom. H), 3.37-3.15 (m, 8H), 2.94 (br, s, 2H, CH$_2$—N), 1.60-1.28 (m, 8H, 4×CH$_2$-hexyl), 0.98-0.89 (m, 3H, CH$_3$-hexyl).

Compound 33.HCl: slightly brown solid; Mp: 75-76° C.; IR (ATR) 3171 cm$^{-1}$ (OH); MS (ESI) m/z 342.4 [M+1]$^+$.

Example 34

3-[2-[(Cyclobutylmethyl)(4-hydroxyphenethyl)amino]ethyl]phenol (Compound 34)

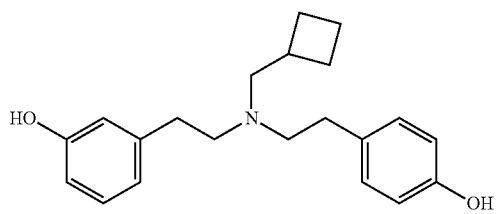

Compound 34

36% yield; $^1$H NMR (CDCl$_3$): δ 7.15 (t, J=7.8 Hz, 2 arom. H), 7.06-7.03 (m, 2 arom. H), 6.78-6.62 (m, 4 arom. H), 2.71-2.62 (m, 10H), 2.09-1.27 (m, 7H).

Compound 34.HCl: white solid. Mp: 102-103° C.; IR (ATR) 3332 cm$^{-1}$ (OH); MS (ESI) m/z 326.4 [M+1]$^+$.

Example 35

3-[2-[(Cyclohexylmethyl)(4-hydroxyphenethyl)amino]ethyl]phenol (Compound 35)

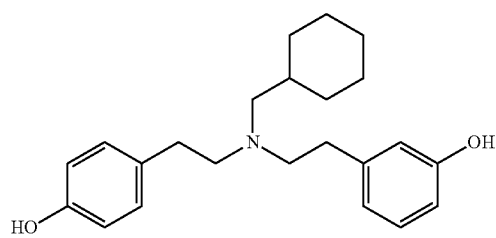

Compound 35

31% yield; $^1$H NMR (CDCl$_3$): δ 7.13 (t, J=7.6 Hz, 2 arom. H), 7.04 (d, J=8.4 Hz, 2 arom. H), 6.77-6.58 (m, 4 arom. H), 2.66 (br, s, 8H), 2.29 (d, J=6.8 Hz, CH$_2$-cyclohexyl), 1.75-0.79 (m, 11H).

Compound 35.HCl: white solid; Mp: 155-157° C.; IR (ATR) 2924 cm$^{-1}$ (OH); MS (ESI) m/z 354.4 [M+1]$^+$.

Example 36

3-[2-[Allyl(4-hydroxyphenethyl)amino]ethyl]phenol (Compound 36)

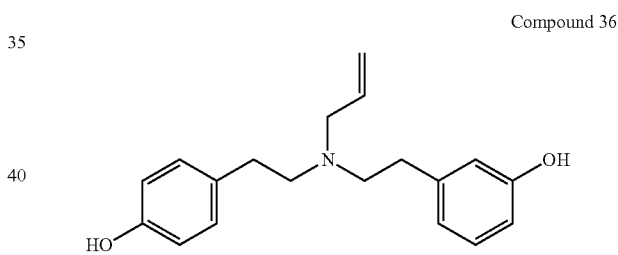

Compound 36

23% yield; $^1$H NMR (CDCl$_3$): δ 7.14 (t, J=7.6 Hz, 2 arom. H), 7.03 (d, J=8 Hz, 2 arom. H), 6.77-6.61 (m, 4 arom. H), 5.97-5.83 (m, 1H olefin), 5.30-5.14 (m, 2H olefin), 3.25 (d, J=6.2 Hz, CH$_2$-olefin), 2.73 (br, s, 8H).

Compound 36.HCl: white solid. Mp: 103-105° C.; IR (ATR) 3195 cm$^{-1}$ (OH); MS (ESI) m/z 298.2 [M+1]$^+$.

General Procedure for the Synthesis of Derivatives 37-39

To a solution of compounds 25, 26 or 28 (0.31 mmol[1]) in 5 mL of CH$_2$Cl$_2$[2] under N$_2$ atmosphere is added BBr$_3$ 1M solution in CH$_2$Cl$_2$ (1.84 mmol) at −15° C.[3]. After 30 min[4] ice and concentrated NH$_4$OH is added and the mixture is stirred at 0° C. for further 30 min. The organic phase is separated and the aqueous layer was extracted with CH$_2$Cl$_2$ (3×20 mL). The combined organic layers are dried over Na$_2$SO$_4$ and evaporated. The resulting oils are purified by column chromatography[5] to give the desired products (compounds 37-39) as transparent oils. The resulting oils are converted into the hydrochloride salts. The hydrochloride salts are obtained by using the following procedure: A part of the obtained oil is dissolved in Et$_2$O and treated with HCl/Et$_2$O[7]. The precipitate is isolated and recrystallized from acetone/Et$_2$O[8] to afford the hydrochloride salt.

Different modifications of this typical procedure are possible, and are commonly known to the skilled artisan, e.g.:
1) The amount can vary from 0.01 mmol to 1000 mol.
2) CH$_2$Cl$_2$ can be replaced by other appropriate solvents.
3) The reaction temperature can vary from −80° C. to 60° C.
4) The reaction time can vary from 0 to 100 hours.
5) The liquid phase for column chromatography can consist of various mixtures of dichloromethane/methanol; or dichloromethane/methanol/ammonia solution; or dichloromethane/methanol/triethylamine; or other appropriate solvents and mixtures thereof.
6) Other appropriate procedures are possible to obtain the hydrochloride salt from the bases. The product can also be isolated by evaporating the reaction mixture. Or the residue can be dissolved in water and freeze dried to obtain a lyophilisate.
7) Recrystallization of the product can be performed by using many different kinds of protic solvents such as alcohols (e.g. methanol, ethanol, isopropanol etc.) and also with different kinds of aprotic solvents such as ethers (diethyl ether, diisopropyl ether etc.), or mixtures of two or more solvents, but also by other appropriate solvents.

Example 37

3-[2-[n-Butyl(4-hydroxyphenethyl)amino]ethyl]phenol (Compound 37)

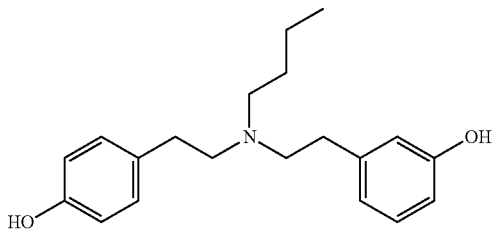

Compound 37

60% yield; $^1$H NMR (DMSO-d$_6$): δ 7.15-7.07 (m, 3 arom. H), 6.76-6.67 (m, 5 arom. H), 3.24-2.98 (m, 10H), 1.69 (br, s, CH$_2$-butyl), 1.38-1.27 (m, 2H, CH$_2$-butyl), 0.95-0.88 (m, 3H, CH$_3$-butyl).

Compound 37.HCl: beige solid; Mp: 65-68° C.; IR (ATR) 2927 cm$^{-1}$ (OH); MS (ESI) m/z 314.4 [M+1]$^+$.

Example 38

3-[2-[(Cyclopropylmethyl)(4-hydroxyphenethyl)amino]ethyl]phenol (Compound 38)

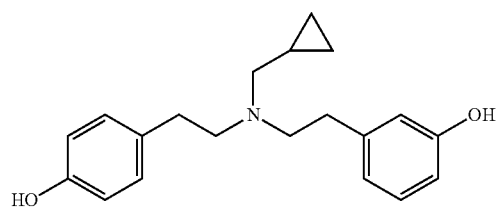

Compound 38

52% yield; $^1$H NMR (CDCl$_3$): δ 7.28-7.03 (m, 4 arom. H), 6.78-6.65 (m, 4 arom. H), 2.85-2.74 (m, 8H), 2.52 (d, J=6.2 Hz, CH$_2$-cyclopropyl), 0.87 (br, s, 2H), 0.53-0.52 (m, 2H), 0.17-0.14 (m, 1H).

Compound 38.HCl: beige solid. Mp: 104-105° C.; IR (ATR) 3017 cm$^{-1}$ (OH); MS (ESI) m/z 312.4 [M+1]$^+$.

Example 39

3,3'-[2,2'-(Cyclopentylmethylazanediyl)bis(ethane-2,1-diyl)]diphenol (Compound 39)

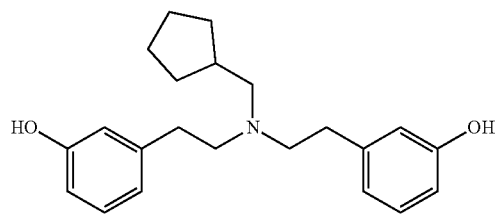

Compound 39

69% yield (transparent oil); $^1$H NMR (CDCl$_3$): δ 7.19-7.10 (m, 3 arom. H), 6.76-6.65 (m, 5 arom. H), 2.75-2.71 (m, 8H), 2.45 (d, J=7.4 Hz, CH$_2$-cyclopentyl), 1.62-1.25 (m, 9H).

Compound 39.HCl as beige solid; Mp: 113° C.; IR (ATR) 2952 cm$^{-1}$ (OH); MS (ESI) m/z 339.4 [M]$^+$.

General Procedure for the Synthesis of Derivatives 40-42

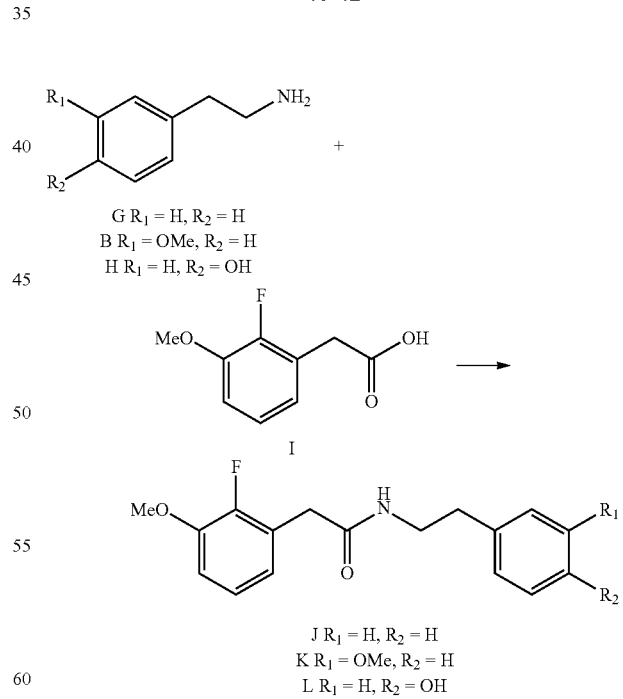

G R$_1$ = H, R$_2$ = H
B R$_1$ = OMe, R$_2$ = H
H R$_1$ = H, R$_2$ = OH

J R$_1$ = H, R$_2$ = H
K R$_1$ = OMe, R$_2$ = H
L R$_1$ = H, R$_2$ = OH

To the stirred solution of starting material (B, G, or H) (1 g, 5.4 mmol[1]), EDCl[2] (985 mg, 7 mmol[1]) and HOAt[3] (0.98 mL, 7 mmol[1]) in anhydrous CH$_2$Cl$_2$[4] (50 mL) under N$_2$, compound I (6.5 mmol[1]) was added at room temperature[5]. The mixture was stirred overnight[6] at room temperature[5], then diluted to 100 mL with CH$_2$Cl$_2$. The organic layer was washed with NaHCO$_3$ sat. (2×30 mL), HCl 0.1 N (2×30 mL), dried over Na$_2$SO$_4$ and evaporated. The resulting oils were purified by column chromatography[7] to give the desired products (compounds J, K and L) as transparent oils. J: $^1$H NMR (CDCl$_3$): δ 7.28-7.21 (m, 3 arom. H), 7.14-6.99 (m, 3 arom. H), 6.93-6. (m, 3 arom. H), 5.51 (br, s, NH), 3.89 (s, CH$_3$O), 3.55-3.52 (m, 2H), 3.48-3.42 (m, 2H), 2.74 (t, J=7.2 Hz, 2H). K: $^1$H NMR (CDCl$_3$): δ 7.28-6.65 (m, 7 arom. H), 5.68 (br, s, NH), 3.88 (s, CH$_3$O), 3.77 (s, CH$_3$O), 3.54 (s, 2H), 3.46 (q, J=6.6 Hz, 2H), 2.73 (t, J=7 Hz, 2H). L: $^1$H NMR (CDCl$_3$): δ 7.28-6.65 (m, 7 arom. H), 5.68 (br, s, NH), 3.88 (s, CH$_3$O), 3.77 (s, CH$_3$O), 3.54 (s, 2H), 3.46 (q, J=6.6 Hz, 2H), 2.73 (t, J=7 Hz, 2H).

To a solution of J, K or L (7.4 mmol[1]) in anhydrous THF (150 mL) is added BH$_3$.THF 1M (37 mL, 37 mmol[1]) under N$_2$ at 0° C.[5]. The reaction mixture is refluxed overnight[6] and then, after cooling, MeOH is added to destroy the excess of BH$_3$. The solvent is evaporated, H$_2$O (100 mL) and NaOH 0.1 N (30 mL) are added. The aqueous phase is extracted with CH$_2$Cl$_2$ (3×20 mL), washed with H$_2$O (3×50 mL) and brine (50 mL), dried over Na$_2$SO$_4$ and evaporated. The resulting oils are purified by column chromatography[7] to give the desired products (compounds 40-42) as transparent oils.

Different modifications of this typical procedure are possible, and are commonly known to the skilled artisan, e.g.:
1) The amount can vary from 0.01 mmol to 1000 mol.
2) Instead of EDCI also other carbodiimides such as N,N'-dicyclohexylcarbodiimide (DCC), N,N'-diisopropylcarbodiimide or other coupling reagents can be used.
3) 1-Hydroxy-7-azabenzotriazol (HOAt) is a coupling reagent which can be substituted by hydroxybenzotriazol (HOBT), 6-chloro-1-hydroxybenzotriazole (Cl-HOBt), (1-[Bis(dimethylamino)methylene]-1H-1,2,3-triazolo[4,5-b]pyridinium-3-oxid hexafluorophosphate) (HATU), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), 3-hydroxy-3,4-dihydro-4-oxo-1,2,3-benzotriazole, N-hydroxy-5-norbornene-2,3-dicarboximide (HONB), N-hydroxysuccinimide or ethyl-2-cyano-2-(hydroxyimino)acetat and others.
4) Other solvents such as tetrahydrofurane, acetonitrile N,N-dimethylformamide or others can be used.
5) The reaction temperature can vary from −80° C. to 160° C.
6) The reaction time can vary from 0 to 500 hours.
7) The liquid phase for column chromatography can consist of various mixtures of dichloromethane/methanol; or dichloromethane/methanol/ammonia solution; or dichloromethane/methanol/triethylamine; or other appropriate solvents and mixtures thereof.

Example 40

1-(2-Fluoro-3-methoxyphenethyl)-2-phenethylamine (Compound 40)

Compound 40

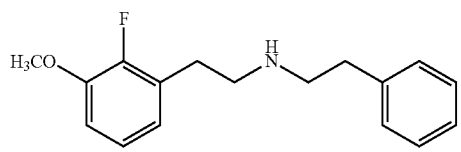

75% yield; $^1$H NMR (CDCl$_3$): δ 7.26-7.13 (m, 5 arom. H), 6.97-6.77 (m, 2 arom. H), 6.68-6.60 (m, 1 arom. H), 3.87 (s, CH$_3$O), 3.14-2.75 (m, 8H).

Example 41

N-(2-Fluoro-3-methoxyphenethyl)-2-(3-methoxyphenyl)ethanamine (Compound 41)

Compound 41

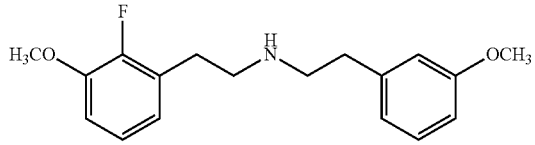

67% yield; $^1$H NMR (CDCl$_3$): δ 7.16-7.12 (m, 1 arom. H), 6.93-6.60 (m, 5 arom. H), 3.87 (s, CH$_3$O), 3.78 (s, CH$_3$O), 3.01-2.87 (m, 8H).

Example 42

4-[2-(2-Fluoro-3-methoxyphenethylamino)ethyl]phenol (Compound 42)

Compound 42

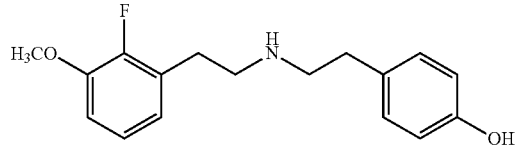

63% yield; $^1$H NMR (CDCl$_3$): δ 6.98-6.84 (m, 4 arom. H), 6.71-6.64 (m, 2 arom. H), 3.89 (s, CH$_3$O), 2.98-2.79 (m, 8H).

General Procedure for the Synthesis of Derivatives 43-48

A mixture of compound 40, 41 or 42 (2.56 mmol[1]), the corresponding alkyl bromide (3.58 mmol[1]), and NaHCO$_3$ (473 mg, 5.6 mmol[2]) was allowed to reflux for 48 h[3] with a catalytic amount of KI in CH$_3$CN[4] (10 mL). The mixture was cooled and filtered, the filtrate was evaporated to dryness, and the crude product was purified by column chromatography[5] to give the desired products (compounds 43-48) as transparent oils.

Different modifications of this typical procedure are possible, and are commonly known to the skilled artisan, e.g.:
1) The amount can vary from 0.01 mmol to 1000 mol.
2) The amount can vary from 0.01 mmol to 5000 mol.
3) The reaction time can vary from 0 to 500 hours.
4) CH$_3$CN can be replaced by other solvents, preferably by acetone, ethanol, methanol, isopropanol, N,N-dimethylformamide, but also by other appropriate solvents.
5) The liquid phase for column chromatography can consist of various mixtures of dichloromethane/methanol; or dichloromethane/methanol/ammonia solution; or dichloromethane/methanol/triethylamine; or other appropriate solvents and mixtures thereof.

Example 43

N-(Cyclobutylmethyl)-N-(2-fluoro-3-methoxyphenethyl)-2-phenylethanamine (Compound 43)

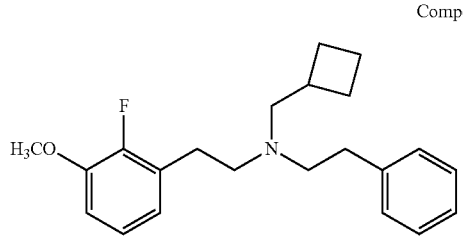

Compound 43

23% yield; $^1$H NMR (CDCl$_3$): δ 7.31-7.18 (m, 5 arom. H), 7.02-6.94 (m, 1 arom. H), 6.86-6.71 (m, 2 arom. H), 3.88 (s, CH$_3$O), 2.77-2.65 (m, 8H), 2.64-2.61 (m, 2H), 2.10-1.64 (m, 7H).

Example 44

N-(Cyclopropylmethyl)-N-(2-fluoro-3-methoxyphenethyl)-2-phenylethanamine (Compound 44)

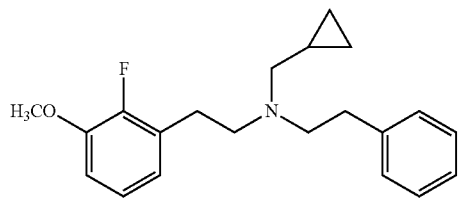

Compound 44

25% yield; $^1$H NMR (CDCl$_3$): δ 7.31-7.21 (m, 4 arom. H), 7.06-6.80 (m, 4 arom. H), 3.87 (s, CH$_3$O), 3.19-3.02 (m, 8H), 2.87 (d, J=6.6 Hz, CH$_2$-cyclopropyl), 0.87-0.63 (m, 4H), 0.40-0.35 (m, 1H).

Example 45

N-(Cyclohexylmethyl)-N-(2-fluoro-3-methoxyphenethyl)-2-phenylethanamine (Compound 45)

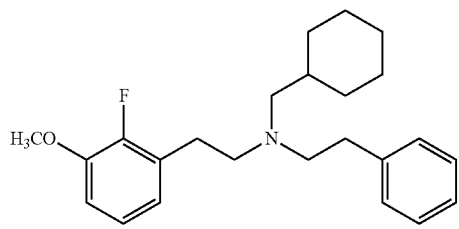

Compound 45

21% yield; $^1$H NMR (CDCl$_3$): δ 7.31-7.10 (m, 5 arom. H), 7.01-6.70 (m, 3 arom. H), 3.88 (s, CH$_3$O), 2.74-2.72 (m, 8H), 2.30 (d, J=8 Hz, CH$_2$-cyclohehyl), 1.89-0.74 (m, 11H).

Example 46

N-Benzyl-N-(2-fluoro-3-methoxyphenethyl)-2-phenylethanamine (Compound 46)

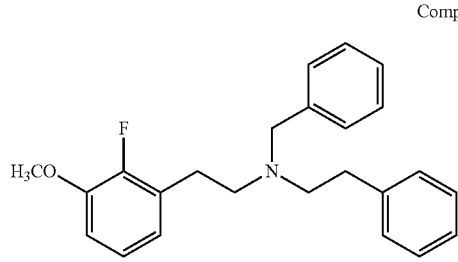

Compound 46

16% yield; $^1$H NMR (CDCl$_3$): δ 7.36-7.12 (m, 9 arom. H), 7.11-6.64 (m, 3 arom. H), 3.89 (s, CH$_3$O), 3.73 (s, CH$_2$-benzyl), 3.67-2.68 (m, 8H).

Example 47

N-(Cyclobutylmethyl)-N-(2-fluoro-3-methoxyphenethyl)-2-(3-methoxyphenyl)ethanamine (Compound 47)

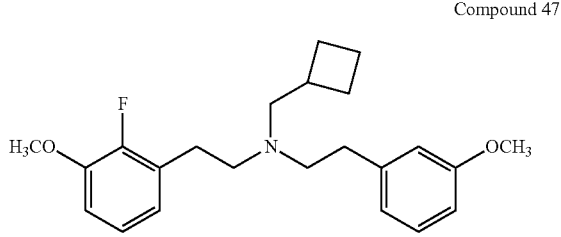 [SMILES: COc1cccc(CCN(CCc2cccc(OC)c2F)CC2CCC2)c1]

Compound 47

21% yield; $^1$H NMR (CDCl$_3$): δ 7.24-7.15 (m, 1 arom. H), 7.01-6.93 (m, 1 arom. H), 6.84-6.71 (m, 5 arom. H), 3.87 (s, CH$_3$O), 3.79 (s, CH$_3$O), 2.77-2.74 (m, 8H), 2.63-2.49 (m, 2H), 2.09-1.64 (m, 7H).

Example 48

4-[2-[(Cyclobutylmethyl)(2-fluoro-3-methoxyphenethyl)amino]ethyl]phenol (Compound 48)

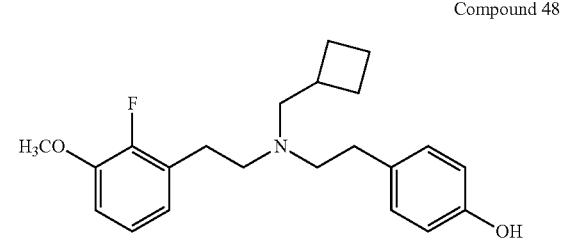 [SMILES: COc1cccc(CCN(CCc2ccc(O)cc2)CC2CCC2)c1F]

Compound 48

18% yield; $^1$H NMR (CDCl$_3$): δ 7.05-6.94 (m, 3 arom. H), 6.85-6.72 (m, 4 arom. H), 3.87 (s, CH$_3$O), 2.80-2.73 (m, 8H), 2.64-2.53 (m, 2H), 2.07-1.66 (m, 7H).

General Procedure for the Synthesis of Derivatives 49-54

To a solution of compounds 43, 44, 45, 46, 47 or 48 (0.54 mmol[1]) in $CH_2Cl_2$[2] (5 mL) under $N_2$ atmosphere is added $BBr_3$ 1M solution in $CH_2Cl_2$ (3.23 mmol) at −15° C.[3]. After 30 min[4] ice and concentrated $NH_4OH$ is added and the mixture is stirred at 0° C. for further 30 min. The organic phase is separated and the aqueous layer was extracted with $CH_2Cl_2$ (3×20 mL). The combined organic layers is dried over $Na_2SO_4$ and evaporated. The resulting oils are purified by column chromatography[5] to give the desired products (compounds 49-54) as transparent oils. The resulting oils are converted into the hydrochloride salts. The hydrochloride salts are obtained by using the following procedure: A part of the obtained oil is dissolved in $Et_2O$ and treated with $HCl/Et_2O$[7]. The precipitate is isolated and recrystallized from acetone/$Et_2O$[8] to afford the hydrochloride salt.

Different modifications of this typical procedure are possible, and are commonly known to the skilled artisan, e.g.:
8) The amount can vary from 0.01 mmol to 1000 mol.
9) $CH_2Cl_2$ can be replaced by other appropriate solvents.
10) The reaction temperature can vary from −80° C. to 60° C.
11) The reaction time can vary from 0 to 100 hours.
12) The liquid phase for column chromatography can consist of various mixtures of dichloromethane/methanol; or dichloromethane/methanol/ammonia solution; or dichloromethane/methanol/triethylamine; or other appropriate solvents and mixtures thereof.
13) Other appropriate procedures are possible to obtain the hydrochloride salt from the bases. The product can also be isolated by evaporating the reaction mixture. Or the residue can be dissolved in water and freeze dried to obtain a lyophilisate.
14) Recrystallization of the product can be performed by using many different kinds of protic solvents such as alcohols (e.g. methanol, ethanol, isopropanol etc.) and also with different kinds of aprotic solvents such as ethers (diethyl ether, diisopropyl ether etc.), or mixtures of two or more solvents, but also by other appropriate solvents.

Example 49

3-[2-[(Cyclobutylmethyl)(phenethyl)amino]ethyl]-2-fluorophenol (Compound 49)

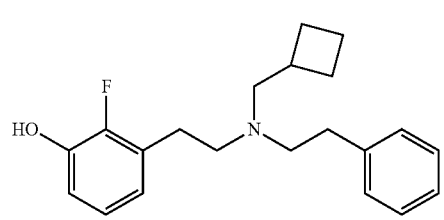

Compound 49

70% yield; $^1$H NMR ($CDCl_3$): δ 7.34-7.18 (m, 5 arom. H), 6.99-6.92 (m, 2 arom. H), 6.77-6.70 (m, 1 arom. H), 2.98 (br, s, 8H), 2.90-2.87 (m, 2H), 2.15-1.26 (m, 7H).
49.HCl: beige solid. Mp 122-124° C.; IR (ATR) 2978 cm$^{-1}$ (OH); MS (ESI) m/z 328.3 [M+1]$^+$.

Example 50

3-[2-[(Cyclopropylmethyl)(phenethyl)amino]ethyl]-2-fluorophenol (Compound 50)

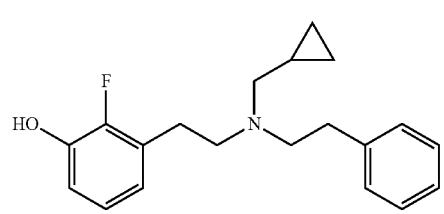

Compound 50

70% yield; $^1$H NMR ($CDCl_3$): δ 7.27-7.20 (m, 7 arom. H), 6.89-6.86 (m, 1 arom. H), 2.92-2.78 (m, 8H), 2.55 (d, =6.2 Hz, $CH_2$-cyclopropyl), 0.95-0.49 (m, 2H), 0.18-0.13 (m, 1H).
50.HCl: beige solid; Mp 120-122° C.; IR (ATR) 2978 cm$^{-1}$ (OH); MS (ESI) m/z 328.3 [M+1]$^+$.

Example 51

3-[2-[(Cyclohexylmethyl)(phenethyl)amino]ethyl]-2-fluorophenol (Compound 51)

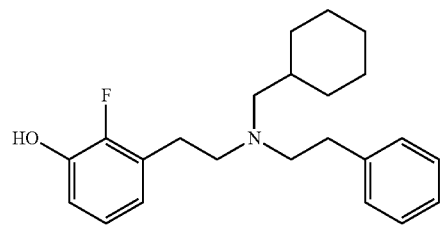

Compound 51

62% yield; $^1$H NMR ($CDCl_3$): δ 7.32-7.16 (m, 5 arom. H), 6.96-6.78 (m, 2 arom. H), 6.71-6.63 (m, 1 arom. H), 2.74 (br, s, 8H), 2.33 (d, J=6.6 Hz, 2H), 1.74-0.80 (m, 11H).
51.HCl: beige solid. Mp: 129-130° C.; IR (ATR) 2924 cm$^{-1}$ (OH); MS (ESI) m/z 356.4 [M+1]$^+$.

Example 52

3-[2-[Benzyl(phenethyl)amino]ethyl]-2-fluorophenol (Compound 52)

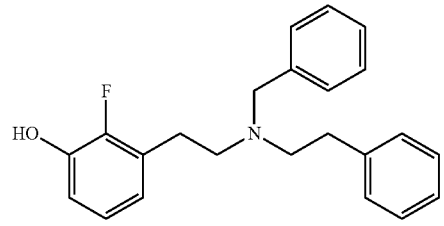

Compound 52

61% yield; $^1$H NMR ($CDCl_3$): δ 7.26-7.11 (m, 9 arom. H), 6.91-6.83 (m, 2 arom. H), 6.65-6.62 (m, 1 arom. H), 3.74 (s, $CH_2$-benzyl), 2.79 (br, s, 8H).

Example 53

3-[2-[(Cyclobutylmethyl)(3-hydroxyphenethyl)amino]ethyl]-2-fluorophenol (Compound 53)

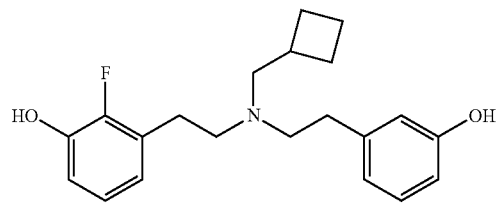

Compound 53

54% yield; $^1$H NMR (DMSO): δ 7.23-7.10 (m, 1 arom. H), 6.92-6.79 (m, 2 arom. H), 6.71-6.59 (m, 3 arom. H), 2.48 (br, s, 4H), 3.08-2.97 (m, 4H), 2.64 (br, s, 2H), 2.10-1.60 (m, 7H).

53.HCl: beige solid. Mp: 130-133° C.; IR (ATR) 2932 cm$^{-1}$ (OH); MS (ESI) m/z 344.3 [M+1]$^+$.

Example 54

3-[2-[(Cyclobutylmethyl)(4-hydroxyphenethyl)amino]ethyl]-2-fluorophenol (Compound 54)

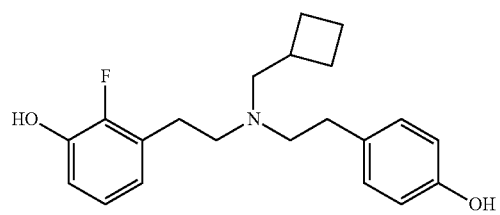

Compound 54

48% yield; $^1$H NMR (DMSO): δ 7.14-7.07 (m, 2 arom. H), 6.96-6.88 (m, 1 arom. H), 6.80-6.71 (m, 3 arom. H), 3.28-3.08 (m, 8H), 2.89 (br, s, 2H), 2.09-1.86 (m, 7H).

54.HCl: beige solid. Mp: 135-136° C.; IR (ATR) 3153 cm$^{-1}$ (OH); MS (ESI) m/z 344.3 [M+1]$^+$.

Example 55

3-[2-[(Cyclobutylmethyl)(phenethyl)amino]ethyl]benzonitrile (Compound 55)

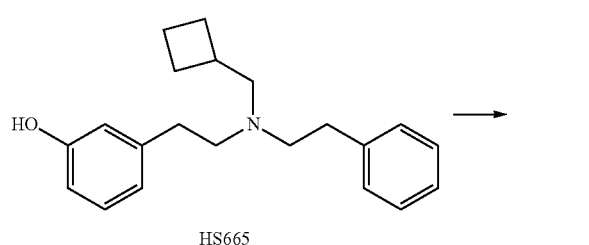

HS665

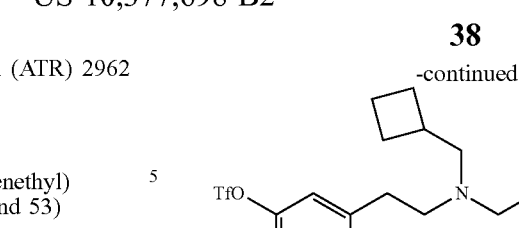

M

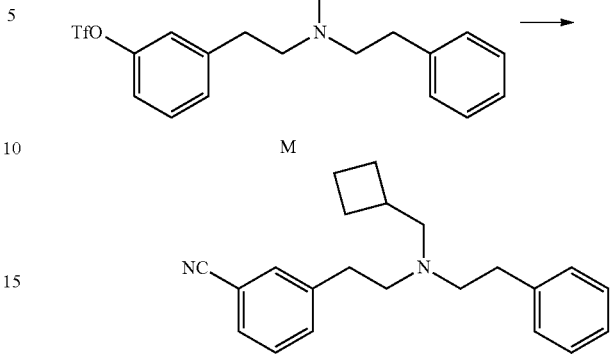

To a mixture of HS665 (Journal of Medicinal Chemistry 2012, 55, pp. 10302-10306) (2 g, 6.46 mmol), pyridine (2.1 mL, 25.84 mmol) and CH$_2$Cl$_2$ (43 mL) was added triflic anhydride (2.17 mL, 12.92 mmol) at 0° C. The mixture was stirred at 0° C. for 2 h, diluted with CH$_2$Cl$_2$ (40 mL), washed with brine (50 mL) and dried over Na$_2$SO$_4$. After removal of the solvent in vacuo, 3-[2-[(cyclobutylmethyl)(phenethyl)amino]ethyl]phenyl trifluoromethanesulfonate (M) (2.65 g, 93%) was obtained as transparent oil: $^1$H NMR (CDCl$_3$): δ 7.26-7.06 (m, 9 arom. H), 3.30-2.97 (m, 10H), 2.81-2.67 (m, 1H), 2.12-1.74 (m, 6H).

A mixture of M (1 g, 2.26 mmol), zinc cyanide (345 mg, 2.94 mmol) and tetrakis(triphenylphosphine)palladium(0) (261 mg, 0.226 mmol), in anhydrous DMF (41 mL) was stirred at 100° C. for 3 h under argon. After cooling to room temperature the reaction mixture was diluted with EtOAc (60 mL) and filtered. The filtrate was washed with NaHCO$_3$ $_{sat}$ (50 mL), H$_2$O (2×30 mL) and brine (50 mL). The organic layer was dried over Na$_2$SO$_4$ and evaporated in vacuo. After column chromatography (silica gel, hexane/EtOAc/NH$_4$OH, 89:10:1) 300 mg (30%) of compound 55 were isolated as yellow oil: IR (ATR) 2228 cm$^{-1}$ (C≡N); $^1$H NMR (CDCl$_3$): δ 7.40-6.99 (m, 9 arom. H), 2.65-2.63 (m, 8H), 2.54-2.47 (m, 2H), 2.41-2.17 (m, 1H) 1.92-1.49 (m, 6H).

Example 56

3-[2-[(Cyclobutylmethyl)(phenethyl)amino]ethyl]benzamide (Compound 56)

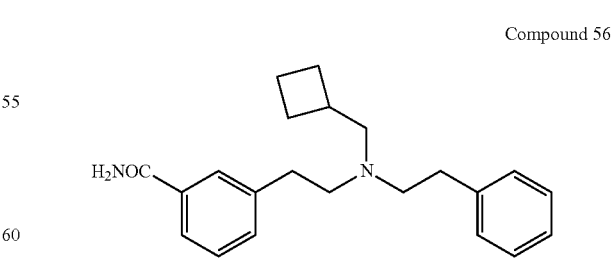

Compound 56

To a solution of compound 55 (280 mg, 0.88 mmol) in t-BuOH (2.8 mL), KOH (148 mg, 2.64 mmol) was added. After the mixture was refluxed for 2 h, the solvent was evaporated and the residue was purified by column chromatography (silica gel, CH$_2$Cl$_2$/MeOH/NH$_4$OH, 98.5:0.5:1) to afford 30 mg (30%) of compound 56 as yellow oil: IR (ATR) 3351 cm$^{-1}$, 3187 cm$^{-1}$ (NH$_2$), 1662 cm$^{-1}$ (CO); $^1$H NMR (CDCl$_3$): δ 7.65-7.59 (m, 2 arom. H), 7.35-7.16 (m, 7 arom. H), 6.03-5.82 (br s, NH$_2$), 2.76-2.74 (m, 8H), 2.61-2.46 (m, 3H), 2.04-1.66 (m, 6H); MS (ESI) m/z 337.28 [M+1]$^+$.

Example 57

N-(Cyclobutylmethyl)-N-phenethyl-2-phenylethanamine (Compound 57)

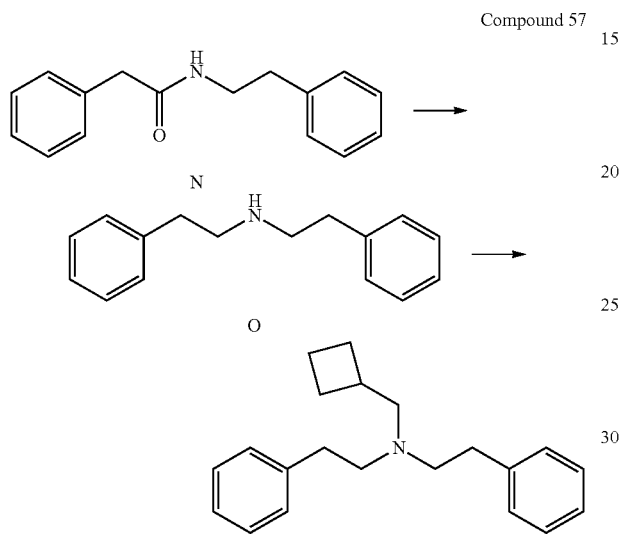

Compound 57

Compound N was synthesized starting from phenylacetic acid and 2-phenylethylamine. To a stirred solution of phenylacetic acid (500 mg, 3.67 mmol$^1$), EDCl$^2$ (915 mg, 4.77 mmol$^1$) and HOAt$^3$ (0.67 mL, 4.77 mmol$^1$) in anhydrous CH$_2$Cl$_2$$^4$ (60 mL), 2-phenylethylamine (0.55 mL, 4.4 mmol$^1$) was added under N$_2$ at room temperature$^5$. The mixture was stirred overnight$^6$ and then diluted to 120 mL with CH$_2$Cl$_2$. The organic layer was washed with NaHCO$_3$ sat. (2×25 mL), HCl 0.1 N (2×25 mL), dried over Na$_2$SO$_4$ and evaporated. The resulting oil was purified by column chromatography$^7$ (silica gel, CH$_2$Cl$_2$/MeOH/NH$_4$OH, 97:2:1) to give 800 mg (91%) of 2-phenyl-N-phenethylacetamide (compound N) as transparent oil: $^1$H NMR (CDCl$_3$): δ 7.35-7.17 (m, 8 arom. H), 7.15-7.00 (m, 2 arom. H), 5.35 (br, s, $^+$NH), 3.53 (s, 2H), 3.46 (q, J=7 Hz, 2H), 2.72 (t, J=7 Hz, 2H).

BH$_3$.THF 1M (16.7 mL, 16.7 mmol$^1$) was added to a solution of compound N (800 mg, 3.34 mmol$^1$) in anhydrous THF (60 mL) under N$_2$ at 0° C.$^5$. The reaction mixture was refluxed overnight$^6$ and then, after cooling, MeOH was added to destroy the excess of BH$_3$. The solvent was evaporated, H$_2$O (70 mL) and NaOH 0.1 N (14 mL) were added. The aqueous phase was extracted with CH$_2$Cl$_2$ (3×80 mL), washed with H$_2$O (3×30 mL), brine (30 mL), dried over Na$_2$SO$_4$ and evaporated. The resulting oil was purified by column chromatography$^7$ (silica gel, CH$_2$Cl$_2$/MeOH/NH$_4$OH, 98:1:1) to give 500 mg (67%) of diphenethylamine (compound O; Journal of Organic Chemistry 1981, 46, pp. 5344-5348: the synthesis described herein for compound O was a hydrogenation procedure of phenylacetonitrile resulting in low yields of compound O) as transparent oil: $^1$H NMR (CDCl$_3$): δ 7.32-7.15 (m, 8 arom. H), 7.08-7.03 (m, 2 arom. H), 3.12-2.74 (m, 8H). This is a new procedure for the synthesis of diphenethylamine.

A mixture of diphenethylamine (O) (700 mg, 3.1 mmol$^1$), cyclobutylmethyl bromide (0.49 mL, 4.35 mmol$^1$), and NaHCO$_3$ (573 mg, 6.82 mmol$^1$) was allowed to reflux for 48 h with a catalytic amount of KI in CH$_3$CN (20 mL). The mixture was cooled and filtered, the filtrate was evaporated to dryness, and the crude product was purified by column chromatography$^7$ (silica gel, CH$_2$Cl$_2$/MeOH/NH$_4$OH, 98:1:1) to give 300 mg (31%) of compound 57 as slightly orange solid: Mp: 96-98° C.; IR (ATR) 2933 cm$^{-1}$ (CH); $^1$H NMR (CDCl$_3$): δ 7.33-7.15 (m, 10 arom. H), 2.83-2.75 (m, 8H), 2.74-2.65 (m, 2H, CH$_2$-cyclobutyl), 2.11-1.81 (m, 7H); MS (ESI) m/z 294.21 [M+1]$^+$.

Different modifications of this typical procedure are possible, and are commonly known to the skilled artisan, e.g.:
1) The amount can vary from 0.01 mmol to 1000 mol.
2) Instead of EDCl also other carbodiimides such as N,N'-dicyclohexylcarbodiimide (DCC), N,N'-diisopropylcarbodiimide or other coupling reagents can be used.
3) 1-Hydroxy-7-azabenzotriazol (HOAt) is a coupling reagent which can be substituted by hydroxybenzotriazol (HOBT), 6-chloro-1-hydroxybenzotriazole (Cl-HOBt), (1-[Bis(dimethylamino)methylene]-1H-1,2,3-triazolo[4,5-b]pyridinium-3-oxid hexafluorophosphate) (HATU), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), 3-hydroxy-3,4-dihydro-4-oxo-1,2,3-benzotriazole, N-hydroxy-5-norbornene-2,3-dicarboximide (HONB), N-hydroxysuccinimide or ethyl-2-cyano-2-(hydroxyimino)acetat and others.
4) Other solvents such as tetrahydrofurane, acetonitrile N,N-dimethylformamide or others can be used.
5) The reaction temperature can vary from −80° C. to 160° C.
6) The reaction time can vary from 0 to 500 hours.
7) The liquid phase for column chromatography can consist of various mixtures of dichloromethane/methanol; or dichloromethane/methanol/ammonia solution; or dichloromethane/methanol/triethylamine; or other appropriate solvents and mixtures thereof.

Example 58

N-(Cyclobutylmethyl)-N-(3-nitrophenethyl)-2-phenylethanamine (Compound 58)

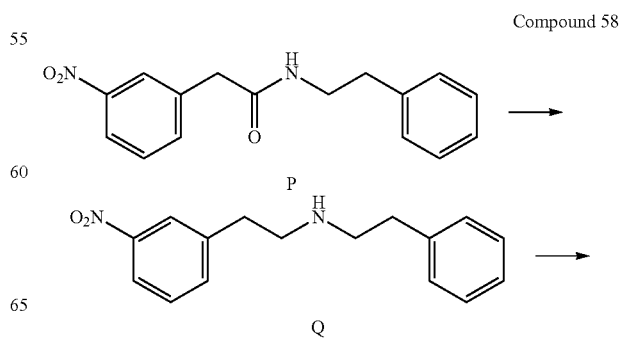

Compound 58

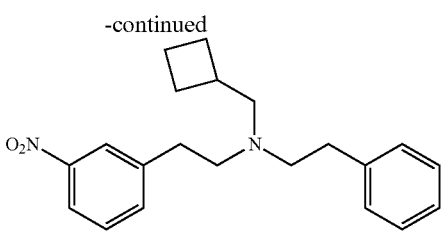

Compound P was synthesized starting from 2-(3-nitrophenyl)acetic acid and 2-phenylethanamine. To a stirred solution of 2-(3-nitrophenyl)acetic acid (3 g, 16.56 mmol[1]), EDCI[2] (4.13 g, 21.53 mmol[1]) and HOAt[3] (3 mL, 21.53 mmol[1]) in anhydrous $CH_2Cl_2$[4] (150 mL), 2-phenylethanamine (2.5 mL, 19.87 mmol[1]) was added under $N_2$ at room temperature[5]. The mixture was stirred overnight[6] then diluted to 250 mL with $CH_2Cl_2$. The organic layer was washed with $NaHCO_3$ sat. (2×50 mL), HCl 0.1 N (2×50 mL), dried over $Na_2SO_4$ and evaporated. The resulting oil was purified by column chromatography[7] (silica gel, $CH_2Cl_2$/MeOH/$NH_4OH$, 98:1:1) to give 3.5 g (74%) of 2-(3-nitrophenyl)-N-phenethylacetamide (P) as a transparent oil: $^1$H NMR ($CDCl_3$): δ 8.13-8.00 (m, 2 arom. H), 7.60-7.43 (m, 2 arom. H), 7.29-7.14 (m, 3 arom. H), 7.10-7.04 (m, 2 arom. H), 5.90 (br, s, $^+$NH), 3.57-3.43 (m, 4H), 2.98-2.86 (m, 1H), 2.84-2.73 (m, 3H). The synthesis of P was described earlier in the U.S. Pat. No. 6,030,985 using the same starting materials but a different procedure.

To a solution of P (3.5 g, 12.31 mmol[1]) in anhydrous THF (100 mL) under $N_2$ was added $BH_3$.THF 1M (61.55 mL, 61.55 mmol[1]) at 0° C.3. The reaction mixture was refluxed overnight[6] and then, after cooling, MeOH was added to destroy the excess of $BH_3$. The solvent was evaporated, $H_2O$ (150 mL) and NaOH 0.1 N (30 mL) were added. The aqueous phase was extracted with $CH_2Cl_2$ (3×150 mL), washed with $H_2O$ (3×60 mL), brine (60 mL), dried over $Na_2SO_4$ and evaporated. The resulting oil was purified by column chromatography[7] to give 930 mg (30%) of compound Q as transparent oil: $^1$H NMR ($CDCl_3$): δ 8.06-8.02 (m, 2 arom. H), 7.50-7.37 (m, 2 arom. H), 7.30-7.14 (m, 5 arom. H), 2.92-2.79 (m, 8H). Compound Q has been prepared from P earlier (U.S. Pat. No. 6,030,985) using a procedure similar to the one described here.

Different modifications of this typical procedure are possible, and are commonly known to the skilled artisan, e.g.:
1) The amount can vary from 0.01 mmol to 1000 mol.
2) Instead of EDCl also other carbodiimides such as N,N'''-dicyclohexylcarbodiimide (DCC), N,N'''-diisopropylcarbodiimide or other coupling reagents can be used.
3) 1-Hydroxy-7-azabenzotriazol (HOAt) is a coupling reagent which can be substituted by hydroxybenzotriazol (HOBT), 6-chloro-1-hydroxybenzotriazole (Cl-HOBt), (1-[Bis(dimethylamino)methylene]-1H-1,2,3-triazolo[4,5-b]pyridinium-3-oxid hexafluorophosphate) (HATU), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), 3-hydroxy-3,4-dihydro-4-oxo-1,2,3-benzotriazole, N-hydroxy-5-norbornene-2,3-dicarboximide (HONB), N-hydroxysuccinimide or ethyl-2-cyano-2-(hydroxyimino)acetat and others.
4) Other solvents such as tetrahydrofurane, acetonitrile N,N-dimethylformamide or others can be used.
5) The reaction temperature can vary from –80° C. to 160° C.
6) The reaction time can vary from 0 to 500 hours.
7) The liquid phase for column chromatography can consist of various mixtures of dichloromethane/methanol; or dichloromethane/methanol/ammonia solution; or dichloromethane/methanol/triethylamine; or other appropriate solvents and mixtures thereof.

A mixture of compound Q (930 mg, 3.44 mmol[1]), cyclobutylmethyl bromide (0.54 mL, 4.82 mmol[1]), and $NaHCO_3$ (636 mg, 7.57 mmol[2]) was allowed to reflux for 48 h[3] with a catalytic amount of KI in $CH_3CN$[4] (23 mL). The mixture was cooled and filtered, the filtrate was evaporated to dryness, and the crude product was purified by column chromatography[5] to give 690 mg (59%) of compound 58 as yellow oil.

IR (ATR) 1528 cm$^{-1}$, 1351 cm$^{-1}$ (NO); $^1$H NMR ($CDCl_3$): δ 8.05-8.01 (m, 2 arom. H), 7.48-7.16 (m, 7 arom. H), 2.86-2.79 (m, 8H), 2.66-2.39 (m, 3H), 2.06-1.60 (m, 6H); MS (ESI) m/z 339.30 [M+1]$^+$.

Different modifications of this typical procedure are possible, and are commonly known to the skilled artisan, e.g.:
1) The amount can vary from 0.01 mmol to 1000 mol.
2) The amount can vary from 0.01 mmol to 5000 mol.
3) The reaction time can vary from 0 to 500 hours.
4) $CH_3CN$ can be replaced by other solvents, preferably by acetone, ethanol, methanol, isopropanol, N,N-dimethylformamide, but also by other appropriate solvents.
5) The liquid phase for column chromatography can consist of various mixtures of dichloromethane/methanol; or dichloromethane/methanol/ammonia solution; or dichloromethane/methanol/triethylamine; or other appropriate solvents and mixtures thereof.

Example 59

3-[2-[(Cyclobutylmethyl)(phenethyl)amino]ethyl]aniline (Compound 59)

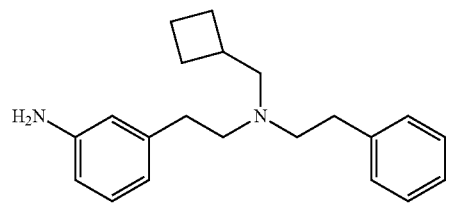

Compound 59

To a solution of compound 58 (50 mg, 0.15 mmol[1]) in EtOH[2] (1 mL), $FeSO_4.7H_2O$ (122 mg, 0.44 mmol[3]), $H_2O$ (0.15 mL) and $NH_4Cl$ (64 mg, 1.2 mmol[3]) were added subsequently, and then zinc powder (29 mg, 0.44 mmol[3]) was added to the mixture. The reaction was carried out for 3 h[4] with an internal temperature of 50° C.[5]. It was then cooled to room temperature and filtered over a pad of Celite. The filter cake was washed with EtOH (5 mL) and the filtrate was concentrated under reduced pressure. To the residue, EtOAc (10 mL) and 25%$_{acq}$. $NH_4Cl$ (5 mL) were added. The biphasic mixture was stirred at room temperature for 5 min and the organic layer was separated. The organic layer was washed with $H_2O$ (10 mL), $NaHCO_3$ $_{sat}$ (10 mL), dried over $Na_2SO_4$ and concentrated under reduced pressure. After column chromatography[6] 25 mg (54%) of compound 59 were obtained as yellow oil: $^1$H NMR (CDCl$_3$): δ 8.05-8.01 (m, 2 arom. H), 7.25-7.10 (m, 5 arom. H), 7.04-6.92 (m, 1 arom. H), 6.54-6.44 (m, 3 arom. H), 2.69-2.65 (m, 8H), 2.58-2.54 (m, 3H), 1.98-1.63 (m, 6H);

A part of the obtained oil of compound 59 was converted into its hydrochloride salt 59.HCl[7,8]: yellowish solid; Mp: 68-70° C.; IR (ATR) 2937 cm$^{-1}$, 2860 cm$^{-1}$ (NH); MS (ESI) m/z 309.27 [M+1]$^+$.

Different modifications of this typical procedure are possible, and are commonly known to the skilled artisan, e.g.:
1) The amount can vary from 0.01 mmol to 10000 mol.
2) Ethanol can be replaced by other protic solvent such as methanol, isopropanol and also other solvents.
3) The amount can vary from 0.01 mmol to 30000 mol.
4) The reaction time can vary from 0 to 500 hours.
5) The reaction temperature can vary from 0° C. to 160° C.
6) The liquid phase for column chromatography can consist of various mixtures of dichloromethane/methanol; or dichloromethane/methanol/ammonia solution; or dichloromethane/methanol/triethylamine; or other appropriate solvents and mixtures thereof.
7) Other appropriate procedures are possible to obtain the hydrochloride salt from the bases. The product can also be isolated by evaporating the reaction mixture. Or the residue can be dissolved in water and freeze dried to obtain a lyophylisate.
8) Recrystallization of the product can be performed by using many different kinds of protic solvents such as alcohols (e.g. methanol, ethanol, isopropanol etc.) and also with different kinds of aprotic solvents such as ethers (diethyl ether, diisopropyl ether etc.), or mixtures of two or more solvents, but also by other appropriate solvents.

Example 60

4-[2-[(Cyclobutylmethyl)(phenethyl)amino]ethyl]phenol (Compound 60)

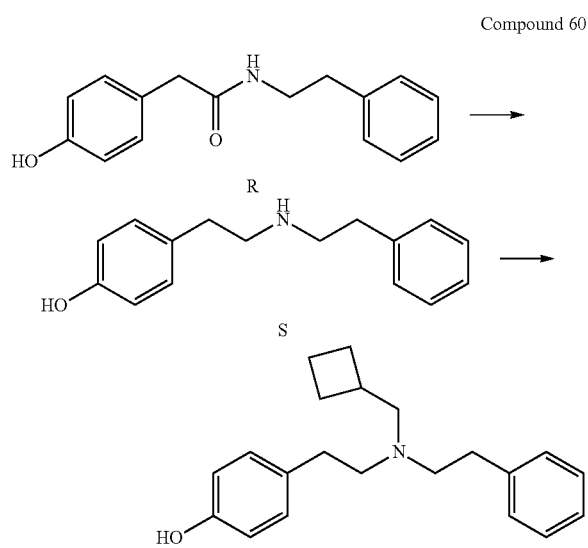

To the stirred solution of 4-hydroxyphenylacetic acid (500 mg, 3.29 mmol[1]), EDCl[2] (818 mg, 4.27 mmol1) and HOAt[3] (7.12 mL, 4.27 mmol[1]) in anhydrous CH$_2$Cl$_2$[4] (66 mL) under N$_2$, 2-phenylethylamine (0.5 mL, 3.95 mmol[1]) was added at room temperature[5]. The mixture was stirred overnight[6] then diluted to 120 mL with CH$_2$Cl$_2$. The organic layer was washed with NaHCO$_3$ sat. (2×25 mL), HCl 0.1 N (2×25 mL), dried over Na$_2$SO$_4$ and evaporated. The resulting oil was purified by column chromatography[7] (silica gel, CH$_2$Cl$_2$/MeOH/NH$_4$OH, 95:4:1) to give 750 mg (89%) of 2-(4-hydroxyphenyl)-N-phenethylacetamide (compound R) as transparent oil: $^1$H NMR (CDCl$_3$) δ 8.36 (br s, $^+$NH), 7.60-7.46 (m, 5 arom. H), 7.34 (d, J=8.8 Hz, 2 arom. H), 7.17 (d, J=8.4 Hz, 2 arom. H), 5.90 (br s, OH), 3.81 (s, CH$_2$CO), 3:32-3:14 (m, NHCH$_2$CH$_2$), 3.10-3.04 (m, NHCH$_2$ CH$_2$).

To a solution of R (700 mg, 2.73 mmol[1]) in anhydrous THF (90 mL) under N$_2$ was added BH$_3$.THF 1M (13.65 mL, 13.65 mmol[1]) at 0° C. The reaction mixture was refluxed overnight then, after cooling, MeOH was added to destroy the excess of BH$_3$. The solvent was evaporated, H$_2$O (70 mL) and NaOH 0.1 N (14 mL) were added. The aqueous phase was extracted with CH$_2$Cl$_2$ (3×80 mL), washed with H$_2$O (3×30 mL), brine (30 mL), dried over Na$_2$SO$_4$ and evaporated. The resulting oil was purified by column chromatography (silica gel, CH$_2$Cl$_2$/MeOH/NH$_4$OH, 97:2:1) to give 470 mg (71%) of compound S: $^1$H NMR (CDCl$_3$) δ 7.26-7.22 (m, 3 arom. H), 7.07-7.04; (m, 2 arom. H); 6.90 (d, J=8.4 Hz, 2 arom. H), 6.68 (d, J=8.2 Hz, 2 arom. H), 3.04-2.80 (m, 8H). Compound S has been prepared earlier by another procedure using different starting materials: H. Pfanz and H. Müller, Patent (1956) DD 11918.

Different modifications of this typical procedure are possible, and are commonly known to the skilled artisan, e.g.:
1) The amount can vary from 0.01 mmol to 1000 mol.
2) Instead of EDCl also other carbodiimides such as N,N'-dicyclohexylcarbodiimide (DCC), N,N'-diisopropylcarbodiimide or other coupling reagents can be used.
3) 1-Hydroxy-7-azabenzotriazol (HOAt) is a coupling reagent which can be substituted by hydroxybenzotriazol (HOBT), 6-chloro-1-hydroxybenzotriazole (Cl-HOBt), (1-[Bis(dimethylamino)methylene]-1H-1,2,3-triazolo[4,5-b]pyridinium-3-oxid hexafluorophosphate) (HATU), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), 3-hydroxy-3,4-dihydro-4-oxo-1,2,3-benzotriazole, N-hydroxy-5-norbornene-2,3-dicarboximide (HONB), N-hydroxysuccinimide or ethyl-2-cyano-2-(hydroxyimino)acetat and others.
4) Other solvents such as tetrahydrofurane, acetonitrile N,N-dimethylformamide or others can be used.
5) The reaction temperature can vary from −80° C. to 160° C.
6) The reaction time can vary from 0 to 500 hours.
7) The liquid phase for column chromatography can consist of various mixtures of dichloromethane/methanol; or dichloromethane/methanol/ammonia solution; or dichloromethane/methanol/triethylamine; or other appropriate solvents and mixtures thereof.

A mixture of compound S (500 mg, 2.07 mmol[1]), cyclobutylmethyl bromide (0.33 mL, 2.9 mmol[1]), and NaHCO$_3$ (383 mg, 4.55 mmol[1]) was allowed to reflux for 48 h[2] in CH$_3$CN[3] (8 mL). The mixture was cooled and filtered, the filtrate was evaporated to dryness, and the crude product was purified by column chromatography[4] (silica gel, CH$_2$Cl$_2$/MeOH/NH$_4$OH, 97.5:1.5:1) to give 176 mg (27%) of compound 60 as yellow oil. A part of the obtained oil of 60 was dissolved in Et$_2$O and treated with HCl/Et$_2$O$^5$. The precipitate was isolated and recrystallized from acetone/Et$_2$O$^6$ to afford 62.HCl: Mp. 157-158° C.; $^1$H NMR (DMSO-d$_6$) δ 7.26-7.22 (m, 5 arom. H), 7.00 (d, J=8.4 Hz, 2 arom. H), 6.64 (d, J=8.4 Hz, 2 arom. H), 3.20-2.83 (m, 11H), 2.01-1.79 (m, 6H); IR (ATR) 3108 (OH); MS (ESI) m/z 309 [M+1]$^+$.

Different modifications of this typical procedure are possible, and are commonly known to the skilled artisan, e.g.:
1) The amount can vary from 0.01 mmol to 1000 mol.
2) The reaction time can vary from 0 to 500 hours.
3) CH$_3$CN can be replaced by other solvents, preferably by acetone, ethanol, methanol, isopropanol, N,N-dimethylformamide, but also by other appropriate solvents.
4) The liquid phase for column chromatography can consist of various mixtures of dichloromethane/methanol; or dichloromethane/methanol/ammonia solution; or dichloromethane/methanol/triethylamine; or other appropriate solvents and mixtures thereof.
5) Other appropriate procedures are possible to obtain the hydrochloride salt from the bases. The product can also be isolated by evaporating the reaction mixture. Or the residue can be dissolved in water and freeze dried to obtain a lyophylisate.
6) Recrystallization of the product can be performed by using many different kinds of protic solvents such as alcohols (e.g. methanol, ethanol, isopropanol etc.) and also with different kinds of aprotic solvents such as ethers (diethyl ether, diisopropyl ether etc.), or mixtures of two or more solvents, but also by other appropriate solvents.

Example 61

4-[2-[(Cyclopentylmethyl)(phenethyl)amino]ethyl]phenol (Compound 61)

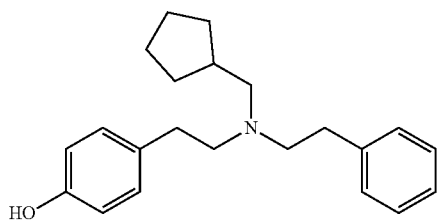

Compound 61

A mixture of compound S (200 mg, 0.83 mmol), cyclopentylmethyl bromide (189 mg, 1.16 mmol), and NaHCO$_3$ (153 mg, 1.83 mmol) was allowed to reflux for 48 h with a catalytic amount of KI in CH$_3$CN (4 mL). The mixture was cooled and filtered, the filtrate was evaporated to dryness, and the crude product was purified by column chromatography (silica gel, CH$_2$Cl$_2$/MeOH/NH$_4$OH, 97:2:1) to give the desired product (compound 61) as yellow oil (60 mg, 22% yield); $^1$H NMR (CDCl$_3$) δ 7.14-7.04 (m, 5 arom. H), 6.92-6.86.00 (m, 2 arom. H), 6.63-6.58 (m, 2 arom. H), 2.71-2.64 (m, 8H), 2.46-2.42 (m, 2H, CH$_2$-cyclopentylmethyl), 2.00-1.93 (m, 1H), 1.61-1.11 (m, 8H).

A part of the obtained oil of compound 61 was dissolved in Et$_2$O and treated with HCl/Et$_2$O. The precipitate was isolated and recrystallized from acetone/Et$_2$O to afford 61.HCl as white solid; Mp: 150-153° C.; IR (ATR) 3126 cm$^{-1}$ (OH); MS (ESI) m/z 324.4 [M+1]$^+$.

Different modifications of this typical procedure are possible (s. example 60).

Example 62

Opioid Receptor Binding, Functional Studies (KOR-Mediated G Protein Activation and KOR-mediated β-Arrestin2 Recruitment) and Analgesic Activity Description of Procedures Opioid Receptor Binding Affinities: Opioid receptor binding studies were performed to determine the binding affinities at human opioid receptors (KOR, MOR and DOR) using membranes from Chinese hamster ovary (CHO) cells expressing one of the human opioid receptors, according to the published procedure (Journal of Medicinal Chemistry 2012, 55, pp. 10302-10306). The KOR, MOR and DOR binding affinities expressed as inhibition constants (K) are presented in Table 1. Inhibition constant (K) values were calculated from competition binding curves using GraphPad Prism program (San Diego, Calif., USA). Binding affinities of compounds of the invention were compared to the affinity of the reference KOR compounds HS665, U50,488 and U69,593 (Table 1).

KOR-mediated G Protein Activation: G protein activation studies using [$^{35}$S]GTPγS binding assays were performed to determine the in vitro pharmacological activities at the KOR with membranes from CHO cells expressing human KOR, according to the published procedure (Journal of Medicinal Chemistry 2012, 55, pp. 10302-10306). Concentration-response curves were constructed, and potency (EC$_{50}$, nM) and efficacy (E$_{max}$, as % of maximum stimulation with respect to the reference KOR agonist U69,593) were calculated using curve fitting analysis with the GraphPad Prism Software. The effect on [$^{35}$S]GTPγS binding produced by compounds of the invention was compared to that of the reference KOR compounds HS665, U50,488 and U69,593 (Table 1). Compounds producing a stimulation of ≥85% are considered to be full agonists, while compounds with stimulation between 20 and 84.9% are partial agonists, and compounds with stimulation below 20% are antagonists.

KOR-mediated β-Arrestin2 Recruitment: To investigate whether the compounds of the present invention are biased against β-arrestin2 recruitment, they were evaluated for their ability to stimulate βarrestin2 recruitment, based on the current knowledge that negative side effects (i.e. sedation, dysphoria, anhedonia, motor incoordination, reduced motivation) result from β-arrestin2-mediated signaling events (Trends in Pharmacological Sciences, 2014, 35, pp 308.316; European Journal of Pharmacology, 2015, 763, pp 184-190). The effect to induce β-arrestin2 recruitment upon KOR activation was investigated using the DiscoveRx PathHunter® eXpress β-arrestin assay (DiscoveRx, Fremont, Calif.), a commonly used assay to assess β-Arrestin2 translocation for 7TM-GPCRs [www.discoverx.com]. The assay was performed using U2OS-hMOR-β-arrestin2 cells according to the manufacturer's protocol [www.discoverx.com]. Concentration-response curves were constructed, and potency (EC$_{50}$, nM) and efficacy (E$_{max}$, as % of maximum stimulation with respect to the reference KOR agonist U69,593) were calculated using curve fitting analysis with the GraphPad Prism Software.

The potency and efficacy for recruiting β-arrestin2 upon binding and activation of the KOR of compounds of the invention were compared to that of the reference KOR compounds HS665, HS666, U50,488 and U69,593 (Table 1). To determine the bias toward KOR-induced G protein signaling over β-arrestin2 recruitment, bias factors were calculated using a similar procedure used to quantify the biased agonism of TRV130, a G protein MOR biased ligand, currently under development for moderate to severe acute pain (Journal of Pharmacology and Experimental Therapeutics 2013, 344, pp 708-717).

Analgesic Activity: Analgesic activity was established in mice after subcutaneous (s.c.) administration using the acetic acid-induced writhing test, according to the described procedure (Journal of Medicinal Chemistry 2012, 55, pp. 10302-10306). The antinociceptive doses ($ED_{50}$) at 30 min after s.c. administration to mice were calculated for compounds of the invention and compared to that of reference KOR compounds HS665, HS666 and U50,488 (Table 2).

KOR compared to the above reference compounds. Remarkably, the compounds according to the present invention display comparable or higher antinociceptive potency than the known full KOR agonists HS665 and U50,488 or the partial KOR agonist HS666. At the same time, β-arrestin2 recruitment by the compounds of the present invention is much lower, while exhibiting a much higher bias factor than the reference compounds HS665, HS666, or U50,488. These characteristics make them particularly suited for the treatment of human disorders where the KOR plays a central role with low propensity for unwanted side effects such as sedation, dysphoria, anhedonia, motor incoordination, reduced motivation, constipation or addictive potential.

TABLE 1

Binding affinities, [$^{35}$S]GTPγS stimulation and β-arrestin2 recruitment of compounds of the invention and reference compounds HS665, HS666, U50,488 and U69,593

| Cpd. No. | Opioid receptor binding assay Affinity $K_i$ (nM)$^a$ | | | G protein assay [$^{35}$S]GTPγS binding KOR$^b$ | | β-arrestin2 recruitment assay$^c$ | | Bias factor$^d$ |
|---|---|---|---|---|---|---|---|---|
| | KOR | MOR | DOR | $EC_{50}$ (nM) | $E_{max}$ (%) | $EC_{50}$ (nM) | $E_{max}$ (%) | |
| 2 | 0.017 | 274 | 5206 | 4.19 | 72.9 | 1342 | 83.0 | 162 |
| 3 | 0.088 | 436 | 2139 | 0.23 | 61.9 | 1359 | 72.2 | 2909 |
| 4 | 0.71 | 463 | 1862 | 4.65 | 79.5 | 4454 | 37.3 | 1172 |
| 12 | 0.34 | 230 | 4184 | 5.51 | 71.4 | n.t. | n.t. | n.t. |
| 27 | 0.17 | 158 | 6238 | 22.8 | 73.6 | n.t. | n.t. | n.t. |
| 29 | 0.18 | 219 | n.t. | 10.6 | 92.2 | n.t. | n.t. | n.t. |
| 39 | 0.38 | 702 | n.t. | 14.2 | 83.6 | n.t. | n.t. | n.t. |
| 49 | 0.022 | 414 | >10000 | 6.90 | 66.1 | 859 | 57.5 | 82 |
| 51 | 0.046 | 543 | >10000 | 2.77 | 84.6 | 4179 | 48.4 | 1514 |
| 53 | 0.12 | 548 | 4748 | 1.49 | 53.1 | 529 | 41.2 | 263 |
| HS665 | 0.49 | 542 | >10000 | 3.62 | 90.0 | 563 | 54.2 | 148 |
| HS666$^e$ | 5.90 | 826 | >10000 | 35.0 | 53.4 | 502 | 25.0 | 18 |
| U50,488 | 0.95 | n.t. | n.t. | 9.31 | 93.0 | n.t. | n.t. | n.t. |
| U69,593 | 1.47 | n.t. | n.t. | 37.1 | 100 | 64.6 | 100 | 1 |

$^a$Determined in competition binding experiments using membranes from CHO cells stably expressing either human KOR, MOR, or DOR.
$^b$Determined in [$^{35}$S]GTPγS binding experiments using CHO-hKOR cell membranes.
$^c$Determined in DiscoveRx PathHunter assay using U2OS-hMOR cells. Efficacy ($E_{max}$, %) is shown as relative to maximum stimulation of the reference KOR agonist U69,593.
$^d$Bias factor was calculated as ratio of the intrinsic relative activity: RAi(β-arrestin2)/RAi(G protein), where RAi = ($E_{max}$ref × $EC_{50}$cpd)/($E_{max}$cpd × $EC_{50}$ref), as described in Journal of Pharmacology and Experimental Therapeutics 2013, 344, pp 708-717. n.t.: not tested ... cpd.: compound tested. ref.: reference ligand (i.e. U69,593).
$^e$HS666: 3-[2-[(Cyclopropylmethyl)(phenethyl)amino]ethyl]phenol Hydrochloride (compound 3 in Journal of Medicinal Chemistry 2012, 55, pp. 10302-10306).

TABLE 2

Antinociceptive potency in the writhing test in mice of compounds of the invention and reference KOR compounds HS665, HS666 and U50,488 after s.c. administration

| Cpd. No. | $ED_{50}$ (mg/kg, s.c.) | Relative analgesic potency to HS665 | Relative analgesic potency to HS666 | Relative analgesic potency to U50,488 |
|---|---|---|---|---|
| 2 | 0.54 | 3.5 | 6.0 | 2.9 |
| 3 | 0.97 | 2.0 | 3.3 | 1.6 |
| 4 | 1.21 | 1.6 | 2.7 | 1.3 |
| 12 | 1.59 | 1.2 | 2.0 | 1.0 |
| 51 | 1.20 | 1.6 | 2.7 | 1.3 |
| HS665 | 1.91 | 1.0 | 1.7 | 0.8 |
| HS666 | 3.23 | 0.6 | 1.0 | 0.5 |
| U50,488 | 1.54 | 1.2 | 2.1 | 1.0 |

The compounds according to the present invention display a high affinity to the KOR that is comparable or higher than the KOR affinity of the reference compounds HS665, HS666, U50,488 or U69,593. Generally, the compounds according to the present invention are either partial or full agonists, with comparable or higher agonist potency at the

What is claimed is:

1. A compound of formula (I),

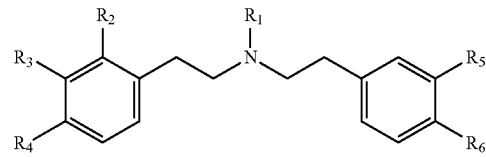

Formula (I)

in which

R$_1$ is selected from C$_2$-C$_{30}$-alkynyl; C$_1$-C$_{30}$-monohydroxyalkyl; C$_2$-C$_{30}$-dihydroxyalkyl; C$_3$-C$_{30}$-trihydroxyalkyl; C$_3$-C$_{12}$-cycloalkyl; C$_4$-C$_{30}$-cycloalkylalkyl; C$_5$-C$_{30}$-cycloalkylalkenyl; C$_5$-C$_{30}$-cycloalkylalkynyl; C$_7$-C$_{30}$-arylalkyl; C$_8$-C$_{30}$-arylalkenyl; C$_8$-C$_{30}$-arylalkynyl;

R$_2$ is hydrogen; F; Cl; I; NO$_2$; CN; SH; CO$_2$H; CONH$_2$; SO$_3$H; SO$_2$NH$_2$; CONHSO$_3$H; NHCONHSO$_2$H; PO$_3$H; PO$_2$H; CF$_3$;

R$_3$ is hydroxy; OCOA, wherein A is selected from C$_1$-C$_6$-alkyl, C$_6$-C$_{14}$-aryl, C$_7$-C$_{16}$-arylalkyl; F; Cl; Br; I; NO$_2$; CN; SH; CO$_2$H; CONH$_2$; SO$_3$H; SO$_2$NH$_2$; CONHSO$_3$H; NHCONHSO$_2$H; PO$_3$H; PO$_2$H; CF$_3$;

R$_4$ is hydrogen; F; Cl; I; NO$_2$; CN; SH; CO$_2$H; CONH$_2$; SO$_3$H; SO$_2$NH$_2$; CONHSO$_3$H; NHCONHSO$_2$H; PO$_3$H; PO$_2$H; CF$_3$;

R$_5$ is hydrogen; hydroxy;

R$_6$ is hydrogen; hydroxy;

with the proviso that R$_1$ cannot be cyclobutylmethyl (CBM) or cyclopropylmethyl (CPM) if R$_3$ is hydroxy and R$_2$, R$_4$, R$_5$ and R$_6$ is hydrogen;

and pharmaceutically acceptable acid addition salts and base addition salts.

2. A compound according to claim 1, wherein

R$_1$ is selected from C$_2$-C$_{12}$-alkynyl; C$_1$-C$_{12}$-monohydroxyalkyl; C$_2$-C$_{12}$-dihydroxyalkyl; C$_3$-C$_{12}$-trihydroxyalkyl; C$_3$-C$_6$-cycloalkyl; C$_4$-C$_{16}$-cycloalkylalkyl; C$_5$-C$_{16}$-cycloalkylalkenyl; C$_5$-C$_{16}$-cycloalkylalkynyl; C$_7$-C$_{16}$-arylalkyl; C$_8$-C$_{16}$-arylalkenyl; C$_8$-C$_{16}$-arylalkynyl;

R$_2$, R$_3$, R$_4$, R$_5$, and R$_6$ are as defined above.

3. A compound of claim 1, wherein

R$_1$ is selected from C$_2$-C$_6$-alkynyl; C$_1$-C$_6$-monohydroxyalkyl; C$_2$-C$_6$-dihydroxyalkyl; C$_3$-C$_6$-trihydroxyalkyl; C$_3$-C$_6$-cycloalkyl; C$_4$-C$_{12}$-cycloalkylalkyl, where cycloalkyl is C$_3$-C$_6$-cycloalkyl and alkyl is C$_1$-C$_6$-alkyl; C$_5$-C$_{12}$-cycloalkylalkenyl, where cycloalkyl is C$_3$-C$_6$-cycloalkyl and alkenyl is C$_2$-C$_6$-alkenyl; C$_5$-C$_{12}$-cycloalkylalkynyl, where cycloalkyl is C$_3$-C$_6$-cycloalkyl and alkynyl is C$_2$-C$_6$-alkynyl; C$_7$-C$_{12}$-arylalkyl where aryl is C$_6$-aryl and alkyl is C$_1$-C$_6$-alkyl; C$_8$-C$_{12}$-arylalkenyl where aryl is C$_6$-aryl and alkenyl is C$_2$-C$_6$-alkyl; C$_8$-C$_{12}$-arylalkynyl where aryl is C$_6$-aryl and alkynyl is C$_2$-C$_6$-alkyl;

R$_2$, R$_3$, R$_4$, R$_5$, and R$_6$ are as defined above.

4. A compound of claim 1, wherein

R$_5$ is hydroxy.

5. A compound selected from:
3-[2-[Allyl(phenethyl)amino]ethyl]phenol
3-[2-[(Cyclopentylmethyl)(phenethyl)amino]ethyl]phenol
3-[2-[(Cyclohexylmethyl)(phenethyl)amino]ethyl]phenol
3-[2-[Benzyl(phenethyl)amino]ethyl]phenol
3-[2-[Propargyl(phenethyl)amino]ethyl]phenol
3-[2-[Isopropyl(phenethyl)amino]ethyl]phenol
3-[2-[Isoamyl(phenethyl)amino]ethyl]phenol
3-[2-[(Cyclobutyl)(phenethyl)amino]ethyl]phenol
N-(Cyclobutylmethyl)-N-(3-methoxyphenethyl)-2-(3-methoxyphenyl)ethanamine
N-(Cyclopropylmethyl)-N-(3-methoxyphenethyl)-2-(3-methoxyphenyl)ethanamine
N-Allyl-N-(3-methoxyphenethyl)-2-(3-methoxyphenyl)ethanamine
3,3'-[2,2'-(Cyclobutylmethylazanediyl)bis(ethane-2,1-diyl)]diphenol
3,3'-[2,2'-(Cyclopropylmethylazanediyl)bis(ethane-2,1-diyl)]diphenol
3,3'-[2,2'-(Allylazanediyl)bis(ethane-2,1-diyl)]diphenol
3-[2-(3-Methoxyphenethylamino)ethyl]phenol
4-[2-(3-Methoxyphenethylamino)ethyl]phenol
3-[2-[(Cyclohexylmethyl)(3-methoxyphenethyl)amino]ethyl]phenol
3-[2-[(Isoamyl)(3-methoxyphenethyl)amino]ethyl]phenol
3-[2-[(n-Butyl)(3-methoxyphenethyl)amino]ethyl]phenol
3-[2-[(n-Pentyl)(3-methoxyphenethyl)amino]ethyl]phenol
3-[2-[(n-Hexyl)(3-methoxyphenethyl)amino]ethyl]phenol
4-[2-[(Cyclobutylmethyl)(3-methoxyphenethyl)amino]ethyl]phenol
4-[2-[(Cyclohexylmethyl)(3-methoxyphenethyl)amino]ethyl]phenol
4-[2-[Allyl(3-methoxyphenethyl)amino]ethyl]phenol
4-[2-[n-Butyl(3-methoxyphenethyl)amino]ethyl]phenol
4-[2-[(Cyclopropylmethyl)(3-methoxyphenethyl)amino]ethyl]phenol
4-[2-[(Cyclopentylmethyl)(3-methoxyphenethyl)amino]ethyl]phenol
3-[2-[(Cyclopentylmethyl)(3-methoxyphenethyl)amino]ethyl]phenol
3,3'-[2,2'-(Cyclohexylmethylazanediyl)bis(ethane-2,1-diyl)]diphenol
3,3'-[2,2'-(Isoamylazanediyl)bis(ethane-2,1-diyl)]diphenol
3,3'-[2,2'-(n-Pentylazanediyl)bis(ethane-2,1-diyl)]diphenol
3,3'-[2,2'-(n-Hexylazanediyl)bis(ethane-2,1-diyl)]diphenol
3,3'-[2,2'-(Cyclopentylmethylazanediyl)bis(ethane-2,1-diyl))]diphenol
3-[2-[(Cyclobutylmethyl)(4-hydroxyphenethyl)amino]ethyl]phenol
3-[2-[(Cyclopropylmethyl)(4-hydroxyphenethyl)amino]ethyl]phenol
3-[2-[(Cyclohexylmethyl)(4-hydroxyphenethyl)amino]ethyl]phenol
3-[2-[Allyl(4-hydroxyphenethyl)amino]ethyl]phenol
3-[2-[n-Butyl(4-hydroxyphenethyl)amino]ethyl]phenol
1-(2-Fluoro-3-methoxyphenethyl)-2-phenethylamine
N-(2-Fluoro-3-methoxyphenethyl)-2-(3-methoxyphenyl)ethanamine
N-(Cyclopropylmethyl)-N-(2-fluoro-3-methoxyphenethyl)-2-phenylethanamine
N-(Cyclobutylmethyl)-N-(2-fluoro-3-methoxyphenethyl)-2-phenylethanamine
4-[2-(2-Fluoro-3-methoxyphenethylamino)ethyl]phenol
N-(Cyclohexylmethyl)-N-(2-fluoro-3-methoxyphenethyl)-2-phenylethanamine
N-Benzyl-N-(2-fluoro-3-methoxyphenethyl)-2-phenylethanamine
N-(Cyclobutylmethyl)-N-(2-fluoro-3-methoxyphenethyl)-2-(3-methoxyphenyl)ethanamine
4-[2-[(Cyclobutylmethyl)(2-fluoro-3-methoxyphenethyl)amino]ethyl]phenol
3-[2-[(Cyclobutylmethyl)(phenethyl)amino]ethyl]-2-fluorophenol
3-[2-[(Cyclopropylmethyl)(phenethyl)amino]ethyl]-2-fluorophenol
3-[2-[(Cyclohexylmethyl)(phenethyl)amino]ethyl]-2-fluorophenol
3-[2-[(Benzyl)(phenethyl)amino]ethyl]-2-fluorophenol
3-[2-[(Cyclobutylmethyl)(3-hydroxyphenethyl)amino]ethyl]-2-fluorophenol
3-[2-[(Cyclobutylmethyl)(4-hydroxyphenethyl)amino]ethyl]-2-fluorophenol
3-[2-[(Cyclobutylmethyl)(phenethyl)amino]ethyl]benzonitrile
3-[2-[(Cyclobutylmethyl)(phenethyl)amino]ethyl]benzamide
N-(Cyclobutylmethyl)-N-phenethyl-2-phenylethanamine
N-(Cyclobutylmethyl)-N-(3-nitrophenethyl)-2-phenylethanamine
3-[2-[(Cyclobutylmethyl)(phenethyl)amino]ethyl]aniline
4-[2-[(Cyclopentylmethyl)(phenethyl)amino]ethyl]phenol 4-[2-[(Cyclobutylmethyl)(phenethyl)amino]ethyl]phenol and pharmaceutically acceptable acid addition salts and base addition salts, esters.

6. A composition comprising a compound of claim 1 together with a pharmaceutically acceptable carrier and/or excipient.

7. A composition comprising a compound of claim 5 together with a pharmaceutically acceptable carrier and/or excipient.

8. A method for the treatment of pain in humans and animals, said method comprising administering a pain treating effective amount of a compound of claim 1 to a human or animal in need thereof.

9. A method for the treatment of pain in humans and animals, said method comprising administering a pain treating effective amount of a compound of claim 5 to a human or animal in need thereof.

10. A method for the treatment of depression in humans and animals, said method comprising administering a depression treating effective amount of a compound of claim 1 to a human or animal in need thereof.

11. A method for the treatment of depression in humans and animals, said method comprising administering a depression treating effective amount of a compound of claim 5 to a human or animal in need thereof.

12. A method for the treatment of water retention, oliguria, dysuria, edemas, pruritus or itching in humans and animals, said method comprising administering an water retention, oliguria, dysuria, edemas, pruritus or itching treating effective amount of a compound of claim 1 to a human or animal in need thereof.

13. A method for the treatment of water retention, oliguria, dysuria, edemas, pruritus or itching in humans and animals, said method comprising administering an water retention, oliguria, dysuria, edemas, pruritus or itching treating effective amount of a compound of claim 5 to a human or animal in need thereof.

\* \* \* \* \*